United States Patent
Fire et al.

(10) Patent No.: US 7,560,438 B2
(45) Date of Patent: *Jul. 14, 2009

(54) GENETIC INHIBITION BY DOUBLE-STRANDED RNA

(75) Inventors: Andrew Fire, Baltimore, MD (US); Stephen Kostas, Chicago, IL (US); Mary Montgomery, St. Paul, MN (US); Lisa Timmons, Lawrence, KS (US); SiQun Xu, Ballwin, MO (US); Hiroaki Tabara, Shizuoka (JP); Samuel E. Driver, Providence, RI (US); Craig C. Mello, Shrewsbury, MA (US)

(73) Assignees: The Carnegie Institution of Washington, Washington, DC (US); The University of Massachusetts, Boston, MA (US)

( * ) Notice: Subject to any disclaimer, the term of this patent is extended or adjusted under 35 U.S.C. 154(b) by 1080 days.

This patent is subject to a terminal disclaimer.

(21) Appl. No.: 10/283,190

(22) Filed: Oct. 30, 2002

(65) Prior Publication Data

US 2003/0051263 A1    Mar. 13, 2003

Related U.S. Application Data

(62) Division of application No. 09/215,257, filed on Dec. 18, 1998, now Pat. No. 6,506,559.

(60) Provisional application No. 60/068,562, filed on Dec. 23, 1997.

(51) Int. Cl.
| | |
|---|---|
| A61K 31/70 | (2006.01) |
| C07H 21/04 | (2006.01) |
| C12N 5/00 | (2006.01) |
| C12N 15/00 | (2006.01) |
| C12Q 1/68 | (2006.01) |
| C12P 19/34 | (2006.01) |

(52) U.S. Cl. ............................ 514/44; 536/23.5; 435/6; 435/91.3; 435/320.1; 435/325

(58) Field of Classification Search .................... 435/6; 514/44; 536/23.1, 24.5
See application file for complete search history.

(56) References Cited

U.S. PATENT DOCUMENTS

| | | | |
|---|---|---|---|
| 3,931,397 A | 1/1976 | Harnden | |
| 4,130,641 A | 12/1978 | Ts'o | |
| 4,283,393 A | 8/1981 | Field | |
| 4,469,863 A | 9/1984 | Ts'o et al. | |
| 4,511,713 A | 4/1985 | Miller et al. | |
| 4,605,394 A | 8/1986 | Skurkovich | |
| 4,766,072 A | 8/1988 | Jendrisak | |
| 4,795,744 A | 1/1989 | Carter | |
| 4,820,696 A | 4/1989 | Carter | |
| 4,945,082 A | 7/1990 | Carter | |
| 4,950,652 A | 8/1990 | Carter | |
| 4,963,532 A | 10/1990 | Carter | |
| 5,024,938 A | 6/1991 | Nozaki | |
| 5,034,323 A | 7/1991 | Jorgensen et al. | |
| 5,063,209 A | 11/1991 | Carter | |
| 5,091,374 A | 2/1992 | Carter | |
| 5,107,065 A | 4/1992 | Shewmaker | |
| 5,132,292 A | 7/1992 | Carter | |
| 5,173,410 A | 12/1992 | Ahlquist | |
| 5,190,931 A | 3/1993 | Inouye | |
| 5,194,245 A | 3/1993 | Carter | |
| 5,208,149 A | 5/1993 | Inouye | |
| 5,258,369 A | 11/1993 | Carter | |
| 5,272,065 A | 12/1993 | Inouye | |
| 5,365,015 A | 11/1994 | Grierson et al. | |
| 5,453,566 A | 9/1995 | Shewmaker | |
| 5,489,519 A * | 2/1996 | Deeley et al. | 435/69.1 |
| 5,514,546 A | 5/1996 | Kool | |
| 5,578,716 A | 11/1996 | Szyf et al. | |
| 5,583,034 A * | 12/1996 | Green et al. | 435/6 |
| 5,593,973 A | 1/1997 | Carter | |
| 5,624,803 A * | 4/1997 | Noonberg et al. | 435/6 |
| 5,631,148 A | 5/1997 | Urdea | |
| 5,643,762 A | 7/1997 | Ohshima et al. | |
| 5,683,985 A | 11/1997 | Chu | |
| 5,683,986 A | 11/1997 | Carter | |
| 5,691,140 A | 11/1997 | Noren et al. | |

(Continued)

FOREIGN PATENT DOCUMENTS

AU    199929163 B2    3/1999

(Continued)

OTHER PUBLICATIONS

Caplen Expert Opin. Biol. Ther. 2003, vol. 3, pp. 575-586.*

(Continued)

*Primary Examiner*—Tracy Vivlemore
(74) *Attorney, Agent, or Firm*—Morgan Lewis Bockius LLP

(57) ABSTRACT

A process is provided of introducing an RNA into a living cell to inhibit gene expression of a target gene in that cell. The process may be practiced ex vivo or in vivo. The RNA has a region with double-stranded structure. Inhibition is sequence-specific in that the nucleotide sequences of the duplex region of the RNA and of a portion of the target gene are identical. The present invention is distinguished from prior art interference in gene expression by antisense or triple-strand methods.

19 Claims, 5 Drawing Sheets

U.S. PATENT DOCUMENTS

| | | | |
|---|---|---|---|
| 5,693,773 | A | 12/1997 | Kandimalla |
| 5,712,257 | A | 1/1998 | Carter |
| 5,738,985 | A | 4/1998 | Miles |
| 5,739,309 | A | 4/1998 | Dattagupta |
| 5,747,338 | A | 5/1998 | Giese |
| 5,795,715 | A | 8/1998 | Livache |
| 5,808,036 | A | 9/1998 | Kool |
| 5,850,026 | A | 12/1998 | DeBonte |
| 5,874,555 | A | 2/1999 | Dervan |
| 5,906,980 | A | 5/1999 | Carter |
| 5,908,779 | A | 6/1999 | Carmichael |
| 5,958,718 | A | 9/1999 | Carter |
| 5,972,704 | A | 10/1999 | Draper et al. ............... 435/375 |
| 6,010,908 | A | 1/2000 | Gruenert et al. |
| 6,022,863 | A | 2/2000 | Peyman ....................... 514/44 |
| 6,130,206 | A | 10/2000 | Carter |
| 6,133,024 | A | 10/2000 | Helene |
| 6,136,601 | A | 10/2000 | Meyer, Jr. et al. |
| 6,291,504 | B1 | 9/2001 | Nugiel |
| 6,369,038 | B1 | 4/2002 | Blumenfeld |
| 6,372,965 | B1 | 4/2002 | Lightner |
| 6,506,559 | B1 | 1/2003 | Fire |
| 6,531,647 | B1 | 3/2003 | Baulcombe |
| 6,573,099 | B2 | 6/2003 | Graham |
| 6,635,805 | B1 | 10/2003 | Baulcombe |
| 2003/0061626 | A1 | 3/2003 | Plaetinck |
| 2004/0138168 | A1 | 7/2004 | Satishchandran |

FOREIGN PATENT DOCUMENTS

| | | |
|---|---|---|
| AU | 1999536778 B2 | 9/1999 |
| AU | 2001195225 | 11/2001 |
| CA | 2012312 | 3/1990 |
| CA | 2370628 | 4/2000 |
| EP | 0318281 A2 | 5/1989 |
| EP | 0325018 A2 | 7/1989 |
| EP | 0347501 A1 | 12/1989 |
| EP | 0213921 B1 | 8/1990 |
| EP | 0495831 B1 | 9/1990 |
| EP | 0286224 B1 | 11/1992 |
| EP | 0350151 B1 | 3/1994 |
| EP | 0303516 B1 | 7/1994 |
| EP | 0306347 B1 | 5/1995 |
| EP | 0465572 B1 | 6/1995 |
| EP | 0281380 | 11/1995 |
| EP | 0308066 B1 | 12/1995 |
| EP | 0300680 B1 | 9/1996 |
| EP | 983370 B1 | 9/2003 |
| GB | 2353282 | 2/2001 |
| GB | 2362885 A | 12/2001 |
| GB | 2377221 B | 8/2004 |
| JP | 09110894 A | 4/1997 |
| JP | 09-227413 | 9/1997 |
| JP | 09227413 A | 9/1997 |
| WO | WO 90/14090 | 5/1989 |
| WO | WO 90/12094 | 10/1990 |
| WO | WO 90/12488 | 11/1990 |
| WO | WO 91/05559 | 5/1991 |
| WO | WO 91/18611 | 12/1991 |
| WO | WO 92/18522 | 10/1992 |
| WO | WO 93/23569 | 11/1993 |
| WO | WO 94/01550 | 1/1994 |
| WO | WO 9401550 A1 * | 1/1994 |
| WO | WO 95/03406 | 2/1995 |
| WO | WO 95/15378 | 6/1995 |
| WO | WO 95/18223 | 7/1995 |
| WO | WO 95/18854 | 7/1995 |
| WO | WO 95/34668 | 12/1995 |
| WO | WO 96/35706 | 11/1996 |
| WO | WO 9635706 A1 | 11/1996 |
| WO | WO 97/10360 | 3/1997 |
| WO | WO 97/11170 | 3/1997 |
| WO | WO 97/44450 | 11/1997 |
| WO | WO 98/05770 | 2/1998 |
| WO | WO 98/53083 | 5/1998 |
| WO | WO 01/70949 | 7/1999 |
| WO | WO 99/32619 | 7/1999 |
| WO | WO 99/49029 | 9/1999 |
| WO | WO 99/53050 | 10/1999 |
| WO | WO 99/61631 | 12/1999 |
| WO | WO 00/01846 | 1/2000 |
| WO | WO 00/63364 | 10/2000 |
| WO | WO 2004/022748 | 3/2004 |

OTHER PUBLICATIONS

Opalinska et al. Nature Reviews Drug Discovery 2002, vol. 1, p. 503-514.*
Jen et al. Stem Cells 2000, vol. 18, p. 307-319.*
Check Nature, 2003, vol. 425, p. 10-12.*
Wightman et al. Cell 1993, vol. 75, pp. 855-862.*
Grishok et al. Cell 2001, vol. 106, pp. 23-34.*
Armstrong et al Neuroscience 2001, vol. 106, pp. 201-216.*
Loseva et al Brain Research 2001, vol. 915, pp. 125-132.*
Platt, Nature 1998, vol. 392 supplement, pp. 11-17.*
Gage, Nature 1998, vol. 392 supplement, pp. 18-24.*
Agrawal, "Antisense Oligonucleotides: Towards Clinical Trials" (1996), *TIBTECH*14: 376-387.
Anderson, "Human Gene Therapy" (1998), *Nature*, 392: 25-30.
Branch, "A Good Antisense Molecule Is Hard to Find" (1998), *TIBS* 23: 45-50.
Clemens et al., Use of Double-Stranded RNA Interference in *Drosophila* Cell Lines to Dissect Signal Transduction Pathways (1999), *PNAS* 97:6499-6503.
Mercola and Cohen, "Antisense Approaches to Cancer Gene Therapy" (1995), *Cancer Gene Therapy* 2: 47-59.
Sharp, "RNAi and Double-Strand RNA" (1999), *Genes & Development* 13: 139-141.
Verma and Somia, "Gene Therapy—Promises, Problems and Prospects" (1997), *Nature* 389: 239-242.
Fire, A., et al., (1998) Potent and specific genetic interference by double-stranded RNA in *Caenorhabditis elegans*. Nature 391: 806-811.
Fire, A., (1998) "RNAi info from the Fire Lab" (Web Document wth protocols to accompany the Fire et al., Nature paper). Posted on our public-access web site from Feb. 1, 1998.
Fire, A., and Fleenor, J. (1998) On the generality of RNA-mediated interference. Worm Breeder's Gazette 15(3): 8 (Jun. 1, 1998).
Montgomery, M., and Fire, A. (1998) Double-stranded RNA as a mediator in sequence-specific genetic silencing and co-suppression. Trends in Genetics 14: 255-258.
Harfe, B., et al. (1998) Analysis of a *Caenorhabditis elegans* twist homolog identifies conserved and divergent aspects of mesodermal patterning. Genes and Development 12: 2623-2635.
Tabara, H., et al. (1998) RNAi in *C. elegans*: Soaking in the genome sequence. Science 282: 430-431.
Timmons, L., and Fire, A. (1998) Specific interference by ingested dsRNA. Nature, 395: 854.
Montgomery, M.K., et al., (1998) RNA as a target of double-stranded RNA-mediated genetic interference in *Caenorhabditis elegan*. Proc. Natl. Acad. Sci. 95:15502-15507.
Fire, A., et al., (1991) Production of antisense RNA leads to effective and specific inhibition of gene expression in *C. elegans* muscle. Development 113: 503-514.
Grieson, D. et al., (1991) Does co-suppression of sense genes in transgenic plants involve antisense RNA? Trends in Biotechnology 9:122-123.
Ratcliff, F., et al., (1997) A similarity between viral defense and gene silencing in plants. Science 276: 1588-1560.
Jorgensen, R.A., et al., (1998) An RNA-based information superhighway in plants. Science 279: 1486-1487.
Waterhouse, P.M., et al., (1998) Virus resistance and gene silencing in plants can be induced by simultaneous expression of sense and antisense RNA. Proc. Natl. Acad. Sci. 95: 13959-13964.

Ngô, H., et al., (1998) Double-stranded RNA induces mRNA degradation in *Trypanosoma brucei* Proc. Natl. Acad. Sci. 95: 14687-14692.

Kennerdell, J., and Carthew, R. (1998) Drosophila frizzled and frizzled2 act in the wingless pathway as determined by dsRNA-medication genetic interference. Cell 95: 1017-1026.

Jorgensen, R.A., et al., (1999) Do unintended artisense transcripts contribute to sense co-suppression in plants? Trends in Genetics 15: 11-12.

Misquitta, L., and Paterson, B.M. (1999) Targeted disruption of gene function in Drosophila by RNA interference (RNA-i): A role for nautilus in embryonic somatic muscle formation. Proc. Natl. Acad. Sci. 96: 1451-1456.

Sharp, P.A. (1999) RNAi and double-stranded RNA. Gene and Development 13: 139-141.

Seydoux, G., et al. (1996) Repression of gene expression in the embryonic germ lineage of *C. elegans*. Nature 382:713-716.

Stam, M., et al. (1997) The silence of genes in transgenic plants. Annals of Botany 79: 3-12.

Nellen, W., and Lichtenstein, C. (1993) What makes an mRNA anti-sense-itive? Trends in Biochemical Sciences 18: 419-423.

Proud, C.G. (1995) PKR: A new name and new roles. Trends in Biochemical Sciences 20: 241-246.

Jacobs, B.L., and Langland, J.O. (1996) When two strands are better than one: The mediators and modulators of the cellular responses to double-stranded RNA. Virology 219: 339-349.

Ratcliff F et al: "A similarity between viral defense and gne silencing in plants", SCIENCE, vol. 276, No. 93, Jun. 6, 1997, pp. 1558-1560, XP002095874, see the whole document.

Fire, A. et al. "Production of antisense RNA leads to effective and specific inhibition of gene expression in *C. elegans* muscle", Development (Cambridge, UK) (1991), 113(2), 503-14 XP002103600 cited in the application, see p. 508, right-hand column, paragraph 2, see p. 509, right-hand column—p. 511, right-hand column, see p. 512, 'Discussion' and figure 7.

Matzke M A et al.: "How and Why Do Plants Inactivate Homologous (Trans) Genes?", Plant Physiology, vol. 107, No. 3, Mar. 1, 1995, pp. 679-685, XP002021174, see p. 680, left-hand column, paragraph 3—right-hand column, paragraph 1, see p. 682.

Fire A et al: "Potent and specific genetic interference by double-stranded RNA in *Caenorhabditis elegans*", NATURE, (Feb. 19, 1998) 391 (6669) 806-11., XP002095876, cited in the application, see the whole document.

Montgomery M K et al: "Double-stranded RNA as a mediator in sequence-specific genetic silencing and co-specific genetic silencing and co—suppression", Trends in Genetics, (Jul. 1998) 14 (7) 255-8., XP004124680, cited in the application, see the whole document.

Timmons L et al: "Specific interference by ingested dsRNA", NATURE, (Oct. 29, 1998) 395 (6705) 854., XP002103601, cited in the application, see the whole document.

Samuel E. Driver, Gregory S. Robinson, Jean Flanagan, Wei Shen, Lois E.H. Smith, David W. Thomas, and Peter C. Roberts, "Oligonucleotide-based inhibition of embryonic gene expression," Nature Biotechnology, vol. 17, Dec. 1999, pp. 1184-1187.

Alejandro Sanchez Alvarado and Phillip A. Newmark, "Double-stranded RNA specifically disrupts gene expression during planarian regeneration," Proc. Natl. Acad. Sci. USA, vol. 96, Apr. 1999, Developmental Biology, pp. 5049-5054.

James D. Thompson, "Shortcuts from gene sequence to function," Nature Biotechnology, vol. 17, Dec. 1999, pp. 1158-1159.

Baum et al., "Inhibition of protein synthesis in reticulocyte lysates by a double-stranded RNA component in HeLa mRNA" Biochem Biophys Res Comm, Jul. 18, 1983, 114:41-49.

Pratt et al., "Regulatin of in vitro translation by double-stranded RNA in mammalian cell mRNA preparations" Nucl Acids Res, Feb. 25, 1988, 16:3497-3510.

Klaff et al., "RNA structure and the regulation of gene expression" Plant Mol Biol, 1996, 32:89-106.

Dolnick, "Naturally occuring antisense RNA" Pharmacol Ther, 1997, 75:179-184.

Wagner et al., "Double-stranded RNA poses puzzle" Nature, Feb. 19, 1998, 391:744-745.

Harbinder et al., "Genetically targeted cell disruption in *Caenorhabditis elegans*" Proc Natl Acad Sci USA, Nov. 1997, 94:13128-131133.

Harcourt et al., "Ebola virus inhibits induction of genes by double-stranded RNA in endothelial cells" Virology, 1998, 252:179-188.

Kumar and Carmichael, "Antisense RNA: Function and fate of duplex RNA in cells of higher eukaryotes" Microbiol Mol Biol Rev, Dec. 1988, 62:1415-1434.

Suzuki et al., "Activation of target-tissue immune-recognition molecules by double-stranded polynucleotides" Proc Natl Acad Sci USA, Mar. 1999, 96:2285-2290.

Hunter, "A touch of elegance with RNAi" Curr. Biol., Jun. 17, 1999, 9:R440-R442.

Tuschi et al., "Targeted mRNA degradation by double-stranded RNA in vitro" Genes Dev, Dec. 15, 1999, 13:3191-3197.

Fire, "RNA-triggered gene silencing" Trends Genet, Sep. 1999, 15:358-363.

Tabara et al., "The rde-1 Gene, RNA interference, and transposon silencing in *C. elegans*" Cell, Oct. 15, 1999, 99:123-132.

Ketting et al., "mut-7 of *C. elegans*, required for transposon silencing and RNA interference, is a homolog of Werner syndrome helicase and RNaseD" Cell, Oct. 15, 1999, 99:133-141.

Bosher et al., "RNA interference can target pre-mRNA: Consequences for gene expression in a *Caenorhabditis elegans* operon" Genetics, Nov. 1999, 153:1245-1256.

Thompson, "Shortcuts from gene Sequence to function" Nature Biotechnology, Dec. 1999, 17:1158-1159.

Driver et al., "Oligonucleotide-based inhibition of embryonic gene expression" Nature Biotechnology, Dec. 1999, 17:1184-1187.

Wargelius et al., "Double-stranded RNA induces specific developmental defects in zebrafish embryos" Biophys Res Comm, 1999, 263:156-161.

Li et al., "Double-stranded RNA injection produces null phenotypes in zebrafish" Development Biology, Jan. 15, 2000, 217:394-405.

Wianny et al., "Specific interference with gene function by double-stranded RNA in early mouse development" Nature Cell Biology, Feb. 2000, 2:70-75.

Catalanotto et al., "Gene silencing in worms and fungi" Nature, Mar. 16, 2000, 404:245.

Hammond et al., "An RNA-directed nuclease mediates post-transcriptional gene silencing in *Drosophila cells*" Nature, Mar. 16, 2000, 404:293-296.

Ketting and Plasterk, "A genetic link between co-suppression and RNA interference in *C. elegans*" Nature, Mar. 16, 2000, 404:296-298.

Grishok et al., "Genetic Requirements for Inheritance of RNAi in *C. elegans*", Science, vol. 287, Mar. 31, 2000, pp. 2494-2497.

Sharp et al., "RNA Interference", Science, vol. 287, Mar. 31, 2000, pp. 2431 and 2433.

Baker et al., "RNAi of the receptor tyrosine phosphatase *Hm*LAR2 in a single cell of an intact embryo leads to growth-cone collapse," Current Biology (2000) vol. 10, pp. 1071-1074.

Bass, "Double-stranded RNA as a template for gene silencing,"Cell (2000) vol. 101, pp. 235-238.

Bastin et al., "Flagellum ontogeny in trypanosomes studied via an inherited and regulated RNA interference sytem," J Cell Science (2000) vol. 113, pp. 3321-3328.

Baulcombe, "Unwinding RNA silencing," Science (2000) vol. 290, pp. 1108-1109.

Bhat et al., "Discs Lost, a novel multi-PDZ domain protein, establishes and maintains epithelial polarity," Cell (1999), vol. 96, pp. 833-845.

Bosher et al., "RNA interference: genetic wand and genetic watchdog," Nature Cell Biology (2000) vol. 2, pp. E31-E36.

Caplen et al., "dsRNA-mediated gen silencing in cultured *Drosophila* cells: a tissue culture model for the analysis of RNA interference," Gene (2000), vol. 252, pp. 95-105.

Chuang et al., "Specific and heritable genetic interference by double-stranded RNA in *Arabidopsis thaliana*," PNAS (2000) vol. 97, pp. 4985-4990.

Colussi et al., "Debcl, a proapoptotic Bcl-2 homologue, is a component of the *Drosophila melanogaster* cell death machinery," J Cell Biology (2000) vol. 148, pp. 703-714.

Denef et al., "Hedgehog induces opposite changes in turnover and subcellular localization of Patched and Smoothened," Cell (2000) vol. 102, pp. 521-531.

Domeier et al., "A link between RNA interference and nonsense-mediated decay in *Caenorhabditis elegans*," Science (2000) vol. 289, pp. 1928-1930.

Fagard et al., "AGO1, ODE-2, and RDE-1 are related proteins required for post-transcriptional gene silencing in plants, quelling in fungi, and RNA interference in animals," PNAS (2000) vol. 97, pp. 11650-11654.

Fortier et al., "Temperature-dependent gene silencing by an expressed inverted repeat in *Drosophila*," Genesis (2000) vol. 26, pp. 240-244.

Fraser et al., "Functional genomic analysis of *C. elegans* chromosome I by systematic RNA interference," Nature (2000) vol. 408, pp. 325-330.

Hill et al., "*dpy-18* Encodes an α-subunit of prolyl-4-hydroxylase in *Caenorhabditis elegans*," Genetics (2000) vol. 155, pp. 1139-1148.

Hsieh et al., "The RING finger/B-Box factor TAM-1 and a retinoblastoma-like protein LIN-35 modulate context-dependent gene silencing in *Caenorhabditis elegans*," Genes & Development (1999) vol. 13, pp. 2985-2970.

Huang et al., "The proneural gene amos promotes multiple dendritic neuron formation in the *Drosophila* peripheral nervous system," Neuron (2000) vol. 25, pp. 57-67.

Hughes et al., "RNAi analysis of *Deformed, proboscipedia* and *Sex combs reduced* in the milkweed bug *Oncopeltus fasciatus*: novel roles for Hox genes in the Hemipteran head," Development (2000) vol. 127, pp. 3683-3694.

Hunter, "Gene silencing: Shrinking the black box of RNAi," Current Biology (2000) vol. 10, pp. R137-R140.

Kennerdell et al., "Heritable gene silencing in *Drosophila* using double-stranded RNA," Nature Biotechnology (2000) vol. 17, pp. 896-898.

Kim et al., "Positioning of longitudinal nerves in *C. elegans* by nidogen," Science (2000) vol. 288, pp. 150-154.

Kostich et al., "Identification and molecular-genetic characterization of a LAMP/CD68-like protein from *Caenorhabditis elegans*," J Cell Science (2000) vol. 113, pp. 2595-2606.

Lam et al., "Inducible expression of double-stranded RNA directs specific genetic interference in *Drosophila*," Current Biology (2000) vol. 10, pp. 957-963.

Lewis et al., "Distinct roles of the homeotic genes Ubx and abd-A in beetle embryonic abdominal appendage development," PNAS (2000) vol. 97, pp. 4504-4509.

Liu et al, "Overlapping roles of two Hox genes and the *exd* ortholog *ceh-20* in diversification of the *C. elegans* postembryonic mesoderm," Development (2000) vol. 127, pp. 5179-5190.

Liu et al., "Essential roles for *Caenorhabditis elegans* lamin gene in nuclear organization, cell cycle progression, and spatial organization of nuclear pore complexes," Molecular Biology Cell (2000) vol. 11, pp. 3937-3947.

Lohmann et al., "Silencing of developmental genes in *Hydra*," Developmental Biology (1999) vol. 214, pp. 211-214.

Maine, "A conserved mechanism for post-transcriptional gene silencing?" Genome Biology (2000) vol. 1, pp. 1018.1-1018.4.

Mette et al., "Transcriptional silencing and promoter methylation triggered by double-stranded RNA," The EMBO Journal (2000) vol. 19, pp. 5194-5201.

Marx, "Interfering with gene expression," Science (2000) vol. 288, pp. 1370-1372.

Melendez et al., "*Caenorhabditis elegans lin-13*, a member of the LIN-35 Rb class of genes involved in vulval development, encodes a protein with zinc fingers and an LXCXE motif," Genetics (2000) vol. 155, pp. 1127-1137.

Nakano et al., "RNA interference for the organizer-specific gene *Xlim-1* in *Xenopus* embryos," Biochemical Biophysical Research Communications (2000) vol. 274, pp. 434-439.

Oates et al., "Too much interference: Injection of double-stranded RNA has nonspecific effects in the zebrafish embryo," Developmental Biology (2000) vol. 224, pp. 20-28.

Oelgeschläger et al., "The evolutionary conserved BMP-binding protein Twisted gastrulation promotes BMP signalling," Nature (2000) vol. 405, pp. 757-763.

Parrish et al., "Functional anatomy of a dsRNA trigger: Differential requirement for the two trigger strands in RNA interference," Molecular Cell (2000) vol. 6, pp. 1077-1087.

Pichler et al., "OOC-3, a novel putative transmembrane protein required for establishment of cortical domains and spindle orientation in the $P_1$ blastomere of *C. elegans* embryos," Development (2000) vol. 127, pp. 2063-2073.

Pineda et al., "Searching for the prototypic eye genetic network: *Sine oculis* is essential for eye regeneration in planarians," PNAS (2000) vol. 97, pp. 4525-4529.

Sawa et al., "Components of the SWI/SNF complex are required for asymmetric cell division in *C. elegans*," Molecular Cell (2000) vol. 6, pp. 617-624.

Shi et al., "Genetic interference in *Trypanosoma brucei* by heritable and inducible double stranded RNA," RNA (2000) vol. 6, pp. 1089-1076.

Shippy et al., "Analysis of *maxillopedia* expression pattern and larval cuticular phenotype in wild-type and mutant Tribolium," Genetics (2000) vol. 155, pp. 721-731.

Stauber et al., "Function of *bicoid* and *hunchback* homologs in the basal cyclorrhaphan fly *Megaselia* (Phoridae)," PNAS (2000) vol. 97, pp. 10844-10849.

Svoboda et al., "Selective reduction of dormat maternal mRNAs in mouse oocytes by RNA interference," Development (2000) vol. 127, pp. 4147-4156.

Tavernarakis et al., "Heritable and inducible genetic interference by double-stranded RNA encoded by transgenes," Nature Genetics (2000) vol. 24, pp. 180-183.

Ui-Tei et al., "Sensitive assay of RNA interference in *Drosophila* and Chinese hamster cultured cells using firefly luciferase gene as target," FEBS Letters (2000) vol. 479, pp. 79-82.

Wang et al., "Inhibition of *Trypanosoma brucei* gene expression by RNA interference using an integratable vector with opposing T7 promoters," J Biological Chemistry (2000) electronically published as Manuscript M008405200, pp. 1-30 and Figures 1-6.

Willert et al., "A *Drosophila axin* homolog, *Daxin*, inhibits Wnt signaling," Development (1999) vol. 126, pp. 4165-4173.

Wu-Scharf et al., "Transgene and Transposon silencing in *Chlamydomonas reinhardtii* by a DEAH-box helicase," Science (2000) vol. 290, pp. 1159-1162.

Yang et al., "Evidence that processed small dsRNAs may mediate sequence-specific mRNA degradation during RNAi in *Drosophila* embryos," Current Biology (2000) vol. 10, pp. 1191-1200.

Zamore et al., "RNAi: Double-stranded RNA directs the ATP-dependent cleavage of mRNA at 21 to 23 nucleotide intervals," Cell (2000) vol. 101, pp. 25-33.

Parrish et al. "Functional anatomy of a dsRNA trigger: Differential requirements for the two trigger strands in RNA interference" Mol. Cell (2000) 6: 1077-1087.

Elbashir et al. "RNA interference is mediated by 21- and 22-nucleotide RNA" Genes Dev. (2001) 15: 188-200.

Elbashir et al. "Duplexes of 21-nucleotide RNAs mediate RNA interference in cultured mammalian cells" Nature (2001) 411: 494-498.

Bass "The short answer" Nature (2001) 411: 428-429.

Davenport "A faster way to shut down genes" Science (2001) 292:1469-1471.

Hutvagner et al. "A cellular function for the RNA-interference enzyme Dicer in the maturation of the *let-7* small temporal RNA" Science (2001) 294: 834-838.

Grishok et al. "Genes and mechanisms related to RNA interference regulate expression of the small temporal RNAs that control *C. elegans* developmental timing" Cell (2001) 106: 23-34.

Caplen et al. "Specific inhibition of gene expression by small double-stranded RNAs in invertebrate and vertebrate systems" Proc Natl Acad Sci USA (2001) early edition pnas. 171251798 pp. 1-6.

Agrawal, Sundhir (1996) "Antisense Oligonucleotides: Towards Clinical Trials" Trends in Biotechnology 14, p. 376.

Akgun, Ercan (1997) "Palindrome Resolution and Recombination in the Mammaliam Germ Line" Molecular and Cellular Biology 17(9): 5559.

Akhtar, S. (1996) "Anti-therapy with antisense oligonucleotides and ribozymes realistic approaches or expensive myths?" Journal of Antimicrobial Chemotherapy p. 159.

Awram P, Gardner RC, Forster RL, Bellamy AR. "The potential of plant viral vectors and transgenic plants for subunit vaccine production" Adv Virus Res. 2002;58:81-124.

Bahner, Ingrid (1996) "Transduction of Human CD34+ Hematopoietic Progenitor Cells by a Retroviral Vector Expressing an RRE Decoy Inhibits Human Immunodeficiency Type 1 Replication in Myelomonocytic Cells Produced in Long-Term Culture" Journal of Virology 70(7): 4352.

Balmori-Melian E, MacDiarmid RM, Beck DL, Gardner RC, Forster RL. "Sequence-, tissue-, and delivery-specific targeting of RNA during post-transcriptional gene silencing" Mol Plant Microbe Interact. Aug. 2002;15(8):753-63.

Barbeau, Benoit (1996) "Characterization of the Human and Mouse Fli-1 promoter regions" BBA Gene Structure and Expression 1307 p. 220.

Baulcombe DC (1996) "Mechanisms of Pathogen-Derived Resistance to Viruses in Transgenic Plants" Plant Cell 8: 1833-1844.

Beck DL, Forster RL, Bevan MW, Boxen KA, Lowe SC. "Infectious transcripts and nucleotide sequence of cloned cDNA of the potexvirus white clover mosaic virus" Virology. Jul. 1990;177(1):152-8.

Beck DL, Guilford PJ, Voot DM, Andersen MT, Forster RL. "Triple gene block proteins of white clover mosaic potexvirus are required for transport" Virology. Aug. 1991;183(2):695-702.

Beck DL, Van Dolleweerd CJ, Lough TJ, Balmori E, Voot DM, Andersen MT, O'Brien IE, Forster RL. "Disruption of virus movement confers broad-spectrum resistance against systemic infection by plant viruses with a triple gene block" Proc Natl Acad Sci U S A. Oct. 25, 1994;91(22):10310-10314.

Betz, Natalie (2003) "RNAi: RNA Interference" RNAi: RNA Interference 83: 33.

Bigler, Jeanette (1995) "Novel Location and Function of a Thyroid Hormone Response Element" The EMBO Journal 14(22): 5710.

Bingham, Paul (1997) "Cosuppression Comes to the Animals" Cell 90: 385.

Bisat, F. N.B.K. Raj and P.M. Pitha (1998) "Differential and Cell Type Expression of Murine Alpha-Interferon Genes is Regulated on the Transcriptional Level" Nucleic Acids Research 16(13): 6067.

Brown, David (1993) "Identification through Overexpression and Tagging of the Variant Type of the Mouse H1e and H1c Genes" The Journal of Biological Chemistry 268(1): 713.

Bryan GT, Gardner RC, Forster RL. (1992) "Nucleotide sequence of the coat protein gene of a strain of clover yellow vein virus from New Zealand: conservation of a stem-loop structure in the 3'region of potyviruses" Arch Virol 124(1-2):133-46.

Buchan et al. (1994) "Characterization of three non-peptide endothelin receptor ligands using human cloned ETA and ETB receptors" Br. J. Pharmacol. 112: 1251-1257.

Chernajovsky, Yuti (1996) "Human Kinesin Light (b) Chain Gene: DNA Sequence and Functional Characterization of Its Promoter and First Exon" DNA and Cell Biology 15:965.

Christy, Robert (1988) "Functional Analysis of the Long Terminal Repeats of Intracisternal A-Particle Genes: Sequences withing the U3 Region Determine Both the Efficiency and Direction of Promoter Activity" Molecular and Cellular Biology 8(3): 1093.

Clusel, Catherine (1993) "Ex Vivo Regulation of Specific Gene Expression by Nanomolar Concentration of Double-Stranded Dumbell Oligonucleotides" Nucleic Acids Research 21(15): 3405.

Clusel, Catherine (1995) "Inhibition of HSV-1 Proliferation by Decoy Phosphodiester Oligonucleotides Containing ICP4 Recognition Sequences" Gene Expression 4: 301.

Decoy, Donald (1995) "Anti sense DNA Down-regulates Protein Kinase C and Enhances Vasopression-stimulated Na Absorption in Rabbit Cortical Collecting Duct" J. Clin. Invest. 95: 2749.

Dobrikova et al. (1996) "T7 DNA-dependent RNA polymerase can transcribe RNA from tick-borne encephalitis virus (TBEV) cDNA with SP6 promoter" FEBS Letters 382, pp. 327-329.

Doughtery WG and Parks TD (1995)"Transgenes and gene supression: telling us something new?" Curr Opin Cell Biol. 7(3):399-405.

Driver SE, Ali M, Mello CC (1996) "Formation of Heritable Anti-Transgenes After RNA Microinjection in *C elegans*" 1996 East Coast Worm Meeting abstract 33.

Driver SE, Ali M, Mello CC (1997) ""Antisense" In *C. elegans* Heritable Gene Silencing Induced By RNA Microinjection" Early 1997 International Worm Meeting abstract 136.

Dronkert, Mies (2000) "Mouse RAD54 Affects DNA Double-Strand Break Repair and Sister Chromatid Exchange" Molecular and Cellular Biology 20(9): 3147.

Dykxhoorn DM et al., (2003) "Killing the messenger: Short RNAs that silence gene expression" Nat Rev. Mol Cell Biol. Jun;4(6):457-67.

Eagles RM, Gardner RC, Forster RL "Nucleotide Sequence of the tamarillo mosaic virus coat protein gene" Nucleic Acids Res. Dec. 11, 1990; 18(23): 7166.

Eagles, R. M., E. Balmori-Melian, D. L. Beck, R. C. Gardner, and R. L. Forster. 1994. "Characterization of NTPase, RNA-binding and RNA-helicase activities of the cytoplasmic inclusion protein of tamarillo mosaic potyvirus" Eur. J. Biochem. 224:677-684.

Elroy-Stein et al. (1990) "Cytoplasmic expression system based on constitutive synthesis of bacteriophage T7 RNA polymerase in mammalian cells" Pro. Natl. Acad. Sci. USA 87, pp. 6743-6747.

Escude, Christophe (1996) "Stable triple helics formed by oligonucleotide N3'—P' phosphoramidates inhibit transcription elongation" Proc. Natl. Acad. Sci. USA 93: 4356.

Everett KR, Milne KS, Forster RL. "Nucleotide sequence of the coat protein genes of strawberry latent ringspot virus: lack of homology to the nepoviruses and comoviruses" J Gen Virol. Jul. 1994;75 ( Pt 7):1821-5.

Faruqi, Tatjana R. (1997) "IFN-y Inhibits Double-Stranded RNA-Induced E-Selectin Expression in Human Endothelial Cells" The Journal of Immunology 159(8): 3989.

Fiaschi, Tania (1997) "The 5'-untranslated Region of the Human Muscle Acylphosphatase m RNA has an Inhibitory Effect on Protein Expression" FEBS Letters 417 No. 1,3 p. 130.

Finkler, Aliza (1992) "Immunity and Resistance to the KP6 Toxin of Ustilago Maydis" MGG 233(3): 395.

Forster RL, Beck DL, Guilford PJ, Voot DM, Van Dolleweerd CJ, Andersen MT. (1992) "The coat Protein of white clover mosaic potexvirus has a role in facilitating cell-to-cell transport in plants" Virology 191(1):480-4.

Forster RL, Bevan MW, Harbison SA, Gardner RC. (1998) "The complete nucleotide sequence of the potex virus white clover mosaic virus" Nucleic Acids Res. 16(1):291-303.

Foster TM, Lough TJ, Emerson SJ, Lee RH, Bowman JL, Forster RL, Lucas WJ. (2002 ) "A surveillance system regulates selective entry of RNA into the shoot apex" Plant Cell. 14(7):1497-508.

Fuerst et al. (1986) "Eukaryotic transient-expression system based on recombinant vaccinia virus that synthesizes bacteriophage T7 RNA polymerase" Pro. Natl. Acad. Sci. USA 83: 8122-8126.

Gao et al. (1997) "Human genes encoding U3 snRNA associate with coiled bodies in interphase cells and are clustered on chromosome 17p11.2 in a complex inverted repeat structure" Nucleic Acids Research 25(23): 4740-4747.

Gardiner SE, Bassett HCM, Noiton DAM, Bus VG, Hofstee ME, White AG, Ball RD, Forster RLS, Rikkerink EHA (1996) "Adetailed linkage map around an apple scab resistance genedemonstrates that two disease resistance classes carry the Vfgene" Theor Appl Genet 93:485-493.

Garrick, David (1998) "Repeat-induced gene silencing in mammals" Nature Genetics 18: 56.

Gervaix, Alain (1997) "Multigene Antiviral Vectors Inhibit Diverse HIV Virus Type 1 Clades" Journal of Virology 71(4): 3048.

Gessani, Sandra (1989) "Activators of Protein Kinase C Enhance Accumulation of Interferon—B mRNA in Murine Cell Lines" Journal of Interferon Reseach 9: 543.

Gimmi, Edward R. (1989) "Alterations in the pre-mRNA topology of the bovine growth hormone polyadenylation region decrease poly (A) site efficiency" Nucleic Acids Research 17(17): 6983.

Giovannangeli, Carine (1996) "Accessibility of nuclear DNA triplex-forming oligonucleotides: The integrated HIV-1 provirus as a target" Proc. Natl. Acad. Sci., USA 94: 79.

Graham, Geoffrey (1990) "RNA Transcripts of the HIV Transactivation Response Element Can Inhibit Action of the Viral Transactivator" Proc. Natl. Acad. Sci. USA 87: 5817.

Graham, Geoffrey (1992) "A Rapid and Reliable Method to Create Tandem Arrays of Short DNA Sequences" Bio Techniques (Research Report) 13(5):780.

Groger, Richard (1989) "Directional antisense and sense cDNA cloning using Epstein-Barr virus episomal expression vectors" Gene (81): 285.

Guilford PJ, Beck DL, Forster RL. (1991) "Influence of the poly(A) tail and putative polyadenylation signal on the infectivity of white clover mosaic potexvirus" Virology 182(1):61-7.

Hacker et al. (1995) "Expression of Sry, the mouse sex determining gene" Development 121, pp. 1603-1614.

Haines, Dale (1991) "Cellular Response to Double-Stranded RNA" Journal of Cellular Biochemistry 46 1991 p. 9.

Harbison SA, Forster RL, Guilford PJ, Gardner RC. (1988) "Organization and interviral homologies of the coat protein gene of white clover mosaic virus" Virology 162(2):459-65.

Harcourt, Brian (1998) "Ebola Virus Inhibits Induction of Genes by Double-Stranded in Endothelial Cells" Virology 252 (article No. VY989446) p. 179.

Helliwell CA, Olive MR, Gebbie L, Forster R, Peacock WJ, Dennis ES (2000) "Isolation of an ent-kaurene oxidase cDNA from Cucurbita maxima" Aust J Plant Physiol 27: 1141-1149.

Henderson, Samuel (1993) "Instability of a Plasmid-Borne Inverted Repeat in *Saccharomyces cerevisiae*" Genetics 133: 57.

Hirashima, Akikazu (1986) "Engineering of the mRNA-interfering complementary RNA immune system against viral infection" Proc. Natl. Acad. Sci. USA 83: 7726.

Sawaki, Hirashima (1989) "Artificial immune system against infection involving antisense RNA targeted to the 5'—terminal noncoding region of coliphage RNA" Journal of Biochemistry 106(1): 163.

Howitt RL, Beever RE, Pearson MN, Forster RL. "Genome characterization of Botrytis virus F, a flexuous rod-shaped mycovirus resembling plant 'potex-like' viruses" J Gen Virol. Jan. 2001;82(Pt 1):67-78.

Imazeki et al. (1988) "Integrated structures of duck hepatitis B virus DNA in hepatocellular carcinoma" Journal of Virology 62(3) 861-865.

Krystal, Geoffrey (1988) "Multiple Mechanisms for Transcriptional Regulation of the myc Gene Family in Small-Cell Lung Cancer" Molecular and Cellular Biology 8(8): 3373.

Krystal, Geoffrey (1990) "N-myc m RNA Forms an RNA-RNA Duplex with Endogenous Antisense Transcripts" Molecular and Cellular Biology 10(8): 4180.

Lee et al. (1993) "The *C. elegans* heterochronic gene lin-4 encodes small RNAs with antisense complementarity to lin-14" Cell 75: 843-854.

Lee, Seok-Woo (1994) "Inhibition of HIV Type 1 in Human T Cells by a potent rev response element decoy consisting of the 13-Nucleotide Minimal Rev-Binding Domain" Journal of Virology 68(12): 8254.

Lee, Seok-Woo (1996) "The Hemagglutinin Genes hagB and hagC of Porphyromonas gingivalis Are Transcribed in Vivo as Shown by Use of a New Expression Vector" Infection and Immunity 64 (11): 4802.

Liefting LW, Andersen MT, Beever RE, Gardner RC, Forster RL. (1996) "Sequence heterogeneity in the two 16S rRNA genes of Phormium yellow leaf phytoplasma" Appl Environ Microbiol. 62(9):3133-9.

Lindbo et al. (1993) "Induction of a Highly Specific Antiviral State in Transgenic Plants: Implications for Regulation of Gene Expression and Virus Resistance" The Plant Cell vol. 5, Issue 12 1749-1759.

Lough TJ, Balmori E, Beck DL, Forster RL. "Western analysis of transgenic plants" Methods Mol. Biol. 1998;81:447-51.

Lough TJ, Emerson SJ, Lucas WJ, Forster RL. "Trans-complementation of long-distance movement of White clover mosaic virus triple gene block (TGB) mutants: phloem-associated movement of TGBp1" Virology. Sep. 15, 2001;288(1):18-28.

Lough TJ, Netzler NE, Emerson SJ, Sutherland P, Carr F, Beck DL, Lucas WJ, Forster RL. "Cell-to-cell movement of potexviruses: evidence for a ribonucleoprotein complex involving the coat protein and first triple gene block protein" Mol Plant Microbe Interact. Sep. 2000;13(9):962-74.

Lough, T.J., Shash, K., Xoconostle-Cazares, B., Hofstra, K.R., Beck, D.L., Balmori, E., Forster, R.L.S., and Lucas, W.J. (1998). "Molecular dissection of the mechanism by which potexvirus triple gene block proteins mediate cell-to-cell transport of infectious RNA" Mol. Plant-Microbe Interact. 11: 801-814.

Mace et al. (1991) "Interferon-regulated viral replication in chronically HIV1-infected promonocytic U937 cells" Research in Virology 142: 213-220.

Matthieu (1992) "Myelin-Deficient Mutant Mice an in Vivo Model for Inhibition of Gene Expression by Natural Antisense RNA" Annals of the New York Academy of Sciences 660: 188.

Mayne, Lynne (1998) "SV40-transformmed normal and DNA-repair deficient human fibroblasts can be transfected with high frequency but retain only amounts of integrated DNA" Gene 66: 65.

McCormack, Stephen (1992) "Mechanism of Interferon Action: Identification of a RNA Binding Domain within the N-terminal Region of the Human RNA-Dependent P1/elF-2a Protein Kinase" Virology 188: 47.

McNair, A.N. B. (1994) "Hepatitis delta virus replication invitro is not affected by interferon -x or -y despite intact cellular responses to interferon and dsRNA" Journal of General Virology 75: 1371.

Mikoshiba, Katshuhiko (1990) "Chimeric and Molecular Genetic Analysis of Myelin-Deficient (Shiverer and Mld) Mutant Mice" Annals of the New York Academy of Sciences 605: 166.

Mikoshiba, Katshuhiko (1990) "Molecular Biology of Myelin Basic Protein Gene Rearrangement and Expression of Anti-Sense RNA in Myelin-Deficient Mutants" Comparative Biochemistry and Physiology 98C(1): 51.

Moore CJ, Sutherland PW, Forster RL, Gardner RC, MacDiarmid RM. "Dark green islands in plant virus infection are the result of posttranscriptional gene silencing" Mol Plant Microbe Interact. Aug. 2001;14(8):939-46.

Morishita, Ryuichi (1996) "Role of Transcriptional cis-Elements, Angiotensinogen Gene Activating Elements, of Angiotensinogen Gene Blood Pressure Regulation" Hypertension 27, 1996 p. 502.

Morris, Kevin (2004) "Small Interfering RNA-Induced Transcriptional Gene Silencing in Human Cells" Science (www.sciencemag.org) 305: 1289.

Nagy, Eszter (1995) "Glyceraldehyde 3-phosphate Dehydrogenase Selectively Binds AU-rich RNA in the NAD +binding Region (Rossmann Fold)*" the Journal of Biochemical Chemistry 270(6): 2755.

Noguchi, Masayuki (1994) "Characterization of an Antisense Inr Element in the eIF-2a Gene" The Journal of Biological Chemistry 269(46): 29161.

Pal-Bhadra, Manika (1997) "Cosupression in Drosophila: Gene Silencing of Alcohol dehydrogenes by white-Adh Transgenes Is Polycomb Dependent" Cell 90, Aug 1997 p. 479.

Palmiter et al. (1984) "Transmission distortion and mosaicism in an unusual transgenic mouse pedigree" Cell 36 pp. 869-877.

Pe'ery, Tsafrira (1997) "Synthesis and Purification of Single-Stranded RNA for use in Experiments with PKR and in Cell-Free Translation Systems" Methods: A Companion to Methods in Enzymology 11, p. 371.

Peyman, John (1997) "Molecular Biology and the Vascular Surgeon" Basic Science of Vascular Disease (Chapter 17): 17.

Podivinsky E, Walton EF, McLeay PL. "Extraction of RNA from kiwi fruit tissues" Biotechniques. Mar. 1994;16(3):396-8.

Raponi, Mitch (2003) "Double-stranded RNA-mediated gene silencing in Fission yeast" Nucleic Acids Research 31(15).

Resnekov, Orna (1989) "RNA Secondary Structure is an Integral Part of the in Vitro Mechanism of Attenuation in Simian Virus 40" The Journal of Biological Chemistry 264(17): 9953.

Reuben et al. (1994) "Cloning and expression of the rabbit gastric CCK-A receptor" Biochimica et Biophysica Actya, 1219: 321-327.

Rocheleau et al. (1997) "Wnt signaling and an APC-related gene specify endoderm in early *C. elegans* embryos" Cell 90(4):707-716.

Rodriguez et al. (1990) "Regulated expression of nuclear genes by T3 RNA polymerase and lac repressor, using recombinant vaccinia virus vectors" Journal of Virology 64(10): 4851-4857.

Roy, Patrice (1990) "Effect of mRNA secondary structure on the efficiency of translational initiation by eukaryotic ribosomes" European Journal of Biochemistry 191(3): 647.

Ruskin, Barbara (1993) "Mutations in POL1 Increase the Mitotic Instability of Tandem Inverted Repeats in *Saccharomyces cerevisiae*," Genetics 133: 43.

Sabl, Joy (1996) "Copy Number and Orientation Determine the Susceptibility of a Gene to Silencing by Nearby Hetreochromatin in Drosophila" Genetics 142, Feb. 1996 p. 447.

Schmitt, Hans Peter (1986) "Characterization of cloned sequences complementary to F9 cell double-stranded RNA and their expression during differentiation" Differentiation 30: 205.

Shaffer, Catherine (2004) "RNAi Shakes up Bio BEO Investor Conference" Biotech News 24(8): 30.

Silverman et al. (1992) "Role of sequences within the first intron in the regulation of expression of eukaryotic initiation factor 2 alpha" The Journal of Biological Chemistry 267(14): 9738-9742.

Simons, Robert (1988) "Naturally occurring antisense RNA control —a brief review" Gene 72: 35.

Smith, Neil (2000) "Total Silencing by inton-spliced hairpin RNAs" Nature 407: 319.

Smolinski, Paula (1995) "Double-Stranded RNA Induces Sickel Erythrocyte Adherence to Endothelium: A Potential Role for Viral Infection in Vaso-Occlusive Pain Episodes in Sickel Cell Anemia" Blood 85(10): 2945.

Smythe, Jason (1995) "Gene therapeutic agents: The use of ribozymes, antisense, and RNA decoys for HIV-1 infection" Inflamm Res 44: 11.

Sonoda, Kengo (1996) "Asymmetric deletion of the junction between the short unique region and the inverted repeat does not affect viral growth in culture and vaccine-induced immunity against Marek's disease" Vaccince 14(4): 277.

Stevenson M (2003) "Dissecting HIV-1 through RNA interference" Nat Rev. Immunol. 3(11):851-8.

Sullenger, Bruce (1990) "Overexpression of TAR Sequence Renders Cells Resistance to HIV Replication" Cell 63: 601.

Sullenger, Bruce (1991) "Analysis of trans-Acting Response Decoy RNA-Mediated Inhibition of HIV Type 1 Transactivation" Journal of Virology vol. 65(12): 6811.

Sun, Lun-Quan (1994) "Ribozyme-mediated suppression of Moloney murine leukemia virus and HIV tyoe I replication in permissive cell lines" Proc. Natl. Acad. Sci USA 91: 9715.

Symington, Lorraine (2002) "Role of RAD52 Epistasis Group Genes in Homologous Recombination and Double-Strand Break Repair" Microbiology and Molecular Biology Reviews 66(4): 630.

Tanaka et al. (1994) "Sequence-specific interaction of alpha-beta-anomeric double-stranded DNA with the p50 subunit of NF kappa B: application to the decoy approach" Nucleic Acids Research 22(15): 3069-3074.

Taylor CB (1997) "Comprehending Cosuppression" Plant Cell 9: 1245-1249.

Tosic, Mirjana (1990) "Post-transcriptional events are responsible for loe expression of myelin basic protein in myelin deficient mice: role of natural antisense RNA"The EMBO Journal 9(2): 401.

Usdin et al. (1993) "SP6 RNA polymerase containing vaccinia virus for rapid expression of cloned genes in tissue culture" BioTechniques 14(2): 222-224.

Van Steeg, Harry (1991) "The translation in vitro of rat ornithine decarboxylase m RNA is blocked by its 5″ untranslated region in a polyamine-independent way" The Biochemical Journal 274: 274.

Volloch, Vladimir Z. (1994) "Evolutionary conserved elements in the 5' untranslated region of B globin mRNA mediate site-specific priming of a unique hairpin structure during cDNA synthesis" Nucleic Acids Rsearch 22(24): 5302.

Wang et al. (1994) "A unusual nucleoporin-related messenger ribonucleic acid is a present in the germ cells of rat testis" Biology of Reproduction 51: 1022-1030.

Wang, Lili (1997) "A factor IX-deficient mouse model for hempphilia B gene therapy" Proc. Natl. Acad. Sci USA, vol. 94: 11563.

Webster DE, Guy PL, Beck DL, Forster RL. (1999) "Distribution and diversity of New Zealand isolates of ryegrass mosaic virus" Arch Virol. 144(10):2059-2064.

Williams, Trevor (1986) "A mouse locus at which transcription from both DNA strands produces mRNAs complementary at their 3' ends" Nature 322: 275.

Wolffe, Alan P. (1997) "Transcription Control: Repressed repeats express themselves" Current Biology 7(12): R796.

Wu, Chaoquin (1994) "Interferon-Stimulated Response Element and NFkB Sites Cooperate to Regulate Double-Stranded RNA-Induced Transcription of the IP-10 Gene" Journal of Interferon Research 14: 357.

Wu, Shiyong (1996) "Double stranded (ds) RNA binding and not Dimerization Correlates with the Activation of the dsRNA-dependent Protein Kinase (PKR)" The Journal of Biochemical Chemistry 271(3): 1756.

Xiong et al. (1995) "Signaling properties of mouse and human corticotroph-releasing factor (CRF) receptors: decreased coupling efficiency of human type II CRF receptor" Endocrionlogy 136(5): 1828-1834.

Yarney et al. (1993) "Molecular cloning and expression of the ovine testicular follicle stimulating hormone receptor" Molecular and Cellular Endocrinology 93: 219-226.

Yu, Mang (1994) "Progress towards gene therapy for HIV infection" Gene Therapy 1: 13.

Zakharyan, R.A. (1986) "Stimulation of Double-Spiral RNA Transformation of Prokaryotic and Eukaryotic Cells" Doklady Akadem: Nauk SSR 288(5): 1251.

Zhenhua, Jin (1991) "Expression of Firefly Luciferase Gene in *Xenopus laevis* oocyte" Chinese Journal of Biotechnology 7(4): 279-284.

Bevec et al., "Constitutive expression of chimeric neo-Rev response element transcripts suppresses HIV-1 replication in human CD4+ T lymphocytes" (1994) *Hum Gene Ther* 5: 193-201.

Cohli et al., "Inhibition of HIV-1 multiplication in a human CD4+ lymphocytic cell line expressing antisense and sense RNA molecules containing HIV-1 packaging signal and Rev response element(s)" (1994) *Antisense Res Dev.* 4: 19-26.

Dorer et al., "Expansions of transgene repeats cause heterochromatin formation and gene silencing in Drosophila" (1994) *Cell* 77: 993-1002.

Dorer et al., "Transgene repeat arrays interact with distant heterochromatin and cause silencing in cis and trans" (1997) *Genetics* 147: 1181-1190.

Lisziewicz et al., "Inhibition of human immunodeficiency virus type 1 replication by regulated expression of a polymeric Tat activation response RNA decoy as a strategy for gene therapy in AIDS" (1993) *Proc Natl Acad Sci* 90: 8000-8004.

Sijen et al., "RNA-Mediated Virus Resistance: Role of Repeated Transgenes and Delineation of Targeted Regions" (1996) *Plant Cell* 8: 2277-2294.

Sun et al., "Resistance to human immunodeficiency virus type 1 infection conferred by transduction of human peripheral blood lymphocytes with ribozyme, antisense, or polymeric transactivation response element constructs" (1995) *Proc Natl Acad Sci* 92: 7272-7276.

Lingelbach et al., Nucleic Acids Res., 16(8):3405-14 (1988).

Liebhaber et al., J. Mol. Biol., 226:609-621 (1992).

Kozak, Mol. cell. Biol., 9(11):5134-12 (1989).

Weaver et al., Proc. Natl. Acad. Sci. USA, 78(7):4073-4077 (Jul. 1981).

Pelletier et al., Cell, 40(3):515-526 (1985).

Watson, Gene, 70(2):399-403 (1988).

Mikoshiba et al., Comp. Biochem. Physiol., 1:51-61 (1991).

Okano et al., Journal of Neurochemistry, 56(2):560-567 (Feb. 1991).

Loomis et al., Antisense Research and Development, 1(3):255-260 (Fall 1991).

Fraser et al., Oncogene, 12(6):1223-1230 (Mar. 1996).

Good et al., Gene Therapy, 41(1):45-54 (Jan. 1997).

Adam, RNAi Inches Toward the Clinic, The Scientist, 18(60 (Mar. 29, 2004).

Lu et al., Abstract No. 338, Keystone Symposia on siRNA and miRNAs, Apr. 14-19, 2004.

Ge et al., Abstract No. 324, Keystone Symposia on siRNAs and miRNAs, Apr. 14-19, 2004.

Hamar et al., Abstract No. 361, Keystone Symposia on siRNAs and miRNAs, Apr. 14-19, 2004.
McCaffrey et al., Abstract No. 039, Keystone Symposia on siRNAs and miRNAs, Apr. 14-19, 2004.
Fuerst et al., Proc. Natl. Acad. Sci. USA, 83:8122-8126 (Nov. 1986).
Rodriguez et al., Journal of Virology, 64(10): 4851-4857 (Oct. 1990).
Elroy-Stein et al., Proc. Natl. Acad. Sci. USA, 87:6743-6747 (Sep. 1990).
Silverman et al., J. of Biological Chemistry, 267(14):9738-9742 (1992).
Noguchi et al., J. of Biological Chemistry, 269(46):29161-29167 (1994).
Yarney et al., Molecular and Cellular Endocrinology, 93:219-226 (1993).
Buchan et al., Br. J. Pharmacol., 112:1251-1257 (1994).
Xiong et al., Endocrinology, 136(5):1828-1834 (May 1995).
Reuben et al., Biochimica et Biophysica Acta, 1219:321-327 (1994).
Kumar et al., Microbiology and Molecular Biology Reviews, 62(4):1415-1434 (Dec. 1998).
Marcus et al., Promega Notes Magazine, 58:36 (1996).
Krystal et al., Molecular and Cellular Biology, 10(8):4180-4191 (Aug. 1990).
Krystal et al., Molecular and Cellular Biology, 8(8):3373-3381 (Aug. 1988).
Nagy et al., J. of Biological Chemistry, 270(6):2755-2763 (1995).
Usdin et al., Biotechniques, 14(2):222-4 (Feb. 1993).
Dobrikova et al., FEBS Lett., 382(3):327-9 (Mar. 18, 1996).
Sorenson et al., J. Mol. Biol. 327:761-766 (2003).
McCaffrey et al., Nature Biotechnol., 21(6):639-44 (2003).
Giladi et al., Mol. Therapy, 8(5):769-76 (2003).
Song et al., Nature Medicine, 9(3):347-51 (Mar. 2003).
Wolff et al., Nonviral Vectors for Cardiovascular Gene Delivery, Ernst Schering Res Found Workshop, 43:41-59 (2003).
Lieberman et al., Trends in Molecular Medicine, 9(9):397-403 (Sep. 2003).
Van Den Haute, et al., Human Gene Therapy, 14:1799-1807 (Dec. 10, 2003).
Rubinson et al., Nature Genetics, 33(3):401-406 (Mar. 2003).
Devroe et al., Expert Opin. Biol. Ther., 4(3):319-327 (2004).
Reich et al., Molecular Vision, 9:210-216 (2003).
Davidson et al., The Lancet, 3:145-149 (Mar. 2004).
Culetto et al., Human Molecular Genetics, 9(6):869-877 (2000).
Tissenbaum et al., Developmental Cell, 1:9-19 (Jan. 2002).
McKay et al., Developmental Cell, 4:131-142 (Jan. 2003).
Berninsone et al., Glycoconjugate Journal, 19:325-330 (2003).
Kurz et al., Nature Rev. Genet., 4(5):380-390 (2003).
Lavery et al., Current Opinion in Drug Discovery & Development, 6(4):561-569 (Jul. 2003).
Agrawal et al., Microbiol. Mol. Biol. Reviews, 67(4):657-685 (2003).
Diallo et al., Oligonucleotides, 13:381-392 (2003).
Gan et al., J. of Neuroscience Methods, 121:151-157 (2002).
Paddison et al., PNAS, 99(3):1443-1448 (Feb. 5, 2002).
Billy et al., PNAS, 98(25):14428-14433 (Dec. 4, 2001).
Yi et al., J. Biol. Chem., 278(2):934-939 (Jan. 10, 2003).
Stipp, Fortune Magazine, published May 12, 2003.
Dr. Nassim Usman, RNAi-2004-Boston Meeting (May 2-4, 2004), Development of siRNA-Based Therapeutics, copy of slide presentation.
Dr. Klaus Giese, RNAi-2004-Boston Meeting (May 2-4, 2004), Short Interfering RNA (siRNA) as New Routes to Therapies, copy of slide presentation.
Dr. Judy Lieberman, RNAi-2004-Boston Meeting (May 2-4, 2004), Silencing the Messenger: Towards In Vivo Delivery, copy of slide presentation.
Dr. Luk Van Parijs, RNAi-2004-Boston Meeting, (May 2-4, 2004) Studying Disease Process Using RNAi, copy of abstract.
Dr. Lata Jayaraman, RNAi-2004-Boston Meeting (May 2-4, 2004), Validation of Novel Drug Targets Using RNAi, copy of slide presentation.

Cameron et al. (1991), "Inhibition of gene expression by a short sense fragment," Nucl Acid Res 19(3):469-475.
Agrawal, Sudhir et al. (1995) "Self-Stabilized Oligonucleotides as Novel Antisense Agents" pp. 105-120. In: Akhtar S, ed. Delivery strategies: antisense oligonucleotide therapeutics. Boca Raton, FL: CRC Press.
Angell, S. M., et al. (1997) "Consistent gene silencing in transgenic plants expressing a replicating potato virus X RNA", EMBO Journal, 16(12), pp. 3675-3684.
Baum, E. Z., et al. (1983) "Inhibition of protein synthesis in reticulocyte lysates by a double-stranded RNA component in HeLa mRNA" Biochem. Biophys. Res. Commun. 114(1), pp. 41-49.
Bhan, P. et al. (1997) "2',5'-Linked oligo-3'-deoxyribonucleoside phosphorothiate chimeras: thermal stability and antisense inhibition of gene expression" Nucleic Acids Research, 25(16), pp. 3310-3317.
Borecky, L., et al. (1981-1982) "Therapeutic use of double-stranded RNAs in man" Tex. Rep. Biol. Med., 41, pp. 575-581.
Cameron, F. H., et al. (1994) "Multiple domains in a ribozyme construct confer increased suppresive activity in monkey cells" Antisense Research and Development, 4(2), pp. 87-94.
Cohli, H., et al. (1994) "Inhibition of HIV-1 multiplication in a human CD4+ lymphocyctic cell line expressing antisense and sense RNA molecules containing HIV-1 packaging signal and Rev response element(s)" Antisense Research and Development, 4(1), pp. 19-26.
Coleman, J., et al. (1984) "The use of RNAs complementary to specific mRNAs to regulate the expression of individual bacterial genes" Cell, 37(2), pp. 429-36.
Dolnick, B. J. (1997) "Naturally occuring antisense RNA" Pharm. Ther. 75(3), pp. 179-184.
Fire, A. et al. (1991) "Production of antisense RNA leads to effective and specific inhibition of gene expression in *C. elegans* muscle" Development, 113(2), pp. 503-514.
Flavell, R. B., (1994) "Inactivation of gene expression in plants as a consequence of specific sequence duplication" Proc. Natl. Acad. Sci. U S A, 91(9), pp. 3490-3496.
Ha, I., Wightman, B., et al. (1996) "A bulged lin-4/lin-14 RNA duplex is sufficient for *Caenorhabditis elegans* lin-14 temporal gradient formation" Genes Dev., 10(23), pp. 3041-3050.
James, W. (1991) "Towards gene-inhibition therapy: a review of progress and prospects in the field of antiviral antisense nucleic acids and ribozymes" Antiviral Chem & Chemother. 2(4), pp. 191-214.
Kibler, K. V., et al, (1997) "Double-stranded RNA is a trigger for apoptosis in vaccinia virus-infected cells" Journal of Virology, 71(3), pp. 1992-2003.
Klaff, P., et al. (1996) "RNA structure and the regulation of gene expression" Plant Mol. Biol. 32(1-2), pp. 89-106.
Manche, L., et al. (1992) "Interactions between double-stranded RNA regulators and the protein kinase DAI" Molecular and Cellular Biology, 12(11), pp. 5238-5248.
Mercola, D., et al. (1995) "Antisense approaches to cancer gene therapy" Cancer Gene Ther. 2(1), pp. 47-59.
Metzlaff, M., et al. (1997) "RNA-mediated RNA degradation and chalcone synthase A silencing in petunia" Cell 88(6), pp. 845-854.
Sarver, N., et al. (1990) "Ribozymes as potential anti-HIV-1 therapeutics agents" Science, 247(4947), pp. 1222-1225.
Sullenger, B. A., et. al. (1990) "Expression of chimeric tRNA-driven antisense transcripts renders NIH 3T3 cells highly resistant to moloney murine leukemia virus replication" Mol. Cell. Biol. 10(12), pp. 6512-6523.
Sullenger, B. A., et. al. (1993) "Tethering ribozymes to a retroviral packaging signal for destruction of viral RNA" Science, 262(5139), pp. 1566-1569.
Uhlmann, E., et. al. (1990) "Antisense oligonucleotides: a new therapeutic principle" Chemical Reviews, 9(4), pp. 544-584.
Yamamoto, R., et al. (1997) "Inhibition of transcription by the TAR RNA of HIV-1 in a nuclear extract of HeLa cells" Nucleic Acids Research, 25(17), pp. 3445-3450.

\* cited by examiner

  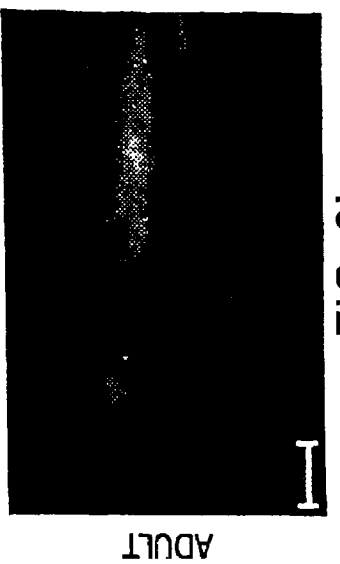
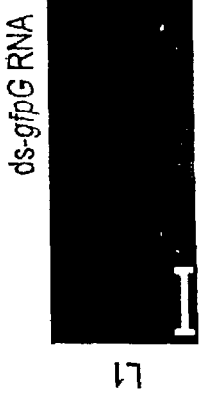 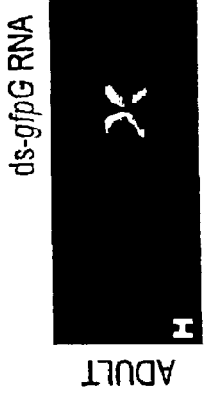 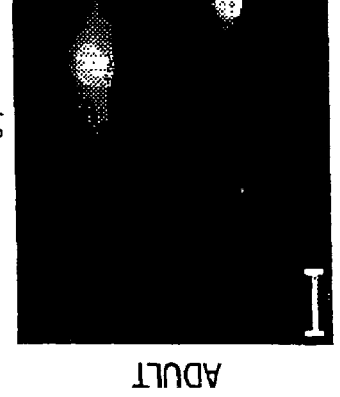
  

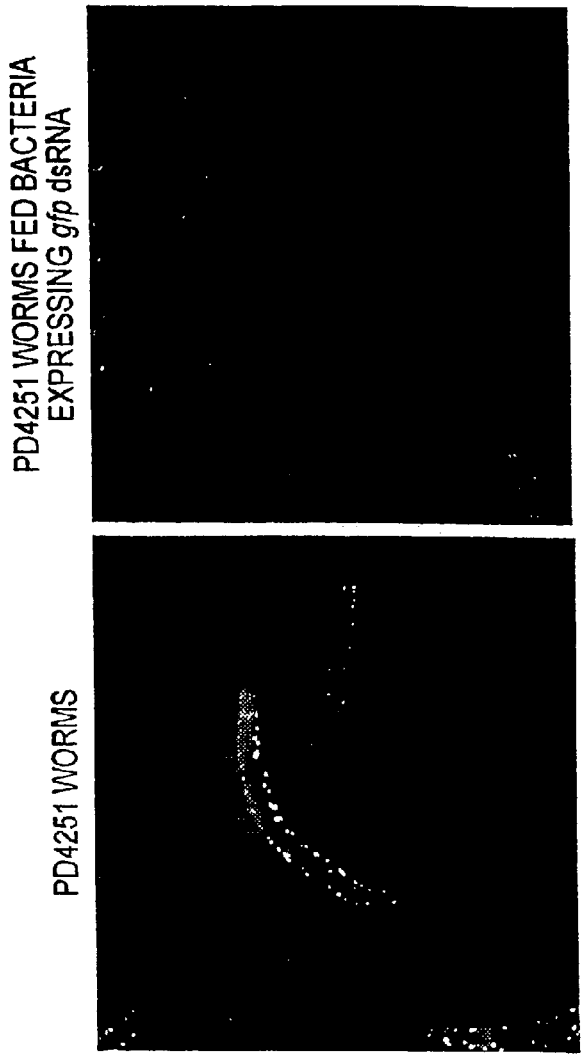
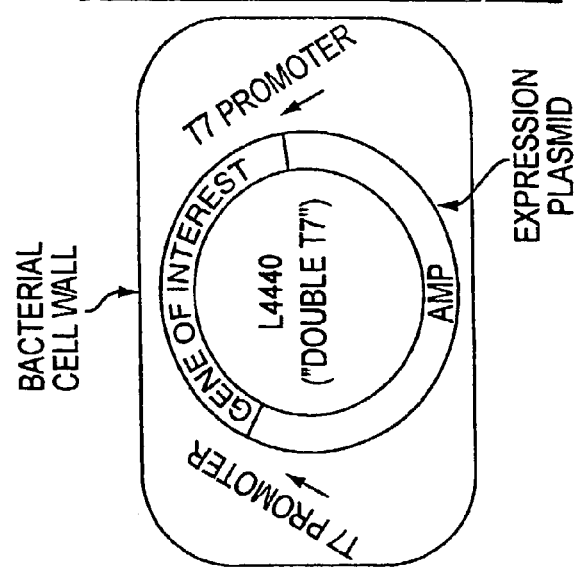
FIG. 5C
FIG. 5B
FIG. 5A

GENETIC INHIBITION BY DOUBLE-STRANDED RNA

RELATED APPLICATION

This application is a divisional application of application Ser. No. 09/215,257, filed Dec. 18, 1998, now U.S. Pat. No. 6,506,559, which claims the benefit of U.S. Provisional Application No. 60/068,562, filed Dec. 23, 1997.

GOVERNMENT RIGHTS

This invention was made with U.S. government support under grant numbers GM-37706, GM-17164, HD-33769 and GM-07231 awarded by the National Institutes of Health. The U.S. government has certain rights in the invention.

BACKGROUND OF THE INVENTION

1. Field of the Invention

The present invention relates to gene-specific inhibition of gene expression by double-stranded ribonucleic acid (dsRNA).

2. Description of the Related Art

Targeted inhibition of gene expression has been a long-felt need in biotechnology and genetic engineering. Although a major investment of effort has been made to achieve this goal, a more comprehensive solution to this problem was still needed.

Classical genetic techniques have been used to isolate mutant organisms with reduced expression of selected genes. Although valuable, such techniques require laborious mutagenesis and screening programs, are limited to organisms in which genetic manipulation is well established (e.g., the existence of selectable markers, the ability to control genetic segregation and sexual reproduction), and are limited to applications in which a large number of cells or organisms can be sacrificed to isolate the desired mutation. Even under these circumstances, classical genetic techniques can fail to produce mutations in specific target genes of interest, particularly when complex genetic pathways are involved. Many applications of molecular genetics require the ability to go beyond classical genetic screening techniques and efficiently produce a directed change in gene expression in a specified group of cells or organisms. Some such applications are knowledge-based projects in which it is of importance to understand what effects the loss of a specific gene product (or products) will have on the behavior of the cell or organism. Other applications are engineering based, for example: cases in which is important to produce a population of cells or organisms in which a specific gene product (or products) has been reduced or removed. A further class of applications is therapeutically based in which it would be valuable for a functioning organism (e.g., a human) to reduce or remove the amount of a specified gene product (or products). Another class of applications provides a disease model in which a physiological function in a living organism is genetically manipulated to reduce or remove a specific gene product (or products) without making a permanent change in the organism's genome.

In the last few years, advances in nucleic acid chemistry and gene transfer have inspired new approaches to engineer specific interference with gene expression. These approaches are described below.

Use of Antisense Nucleic Acids to Engineer Interference

Antisense technology has been the most commonly described approach in protocols to achieve gene-specific interference. For antisense strategies, stochiometric amounts of single-stranded nucleic acid complementary to the messenger RNA for the gene of interest are introduced into the cell. Some difficulties with antisense-based approaches relate to delivery, stability, and dose requirements. In general, cells do not have an uptake mechanism for single-stranded nucleic acids, hence uptake of unmodified single-stranded material is extremely inefficient. While waiting for uptake into cells, the single-stranded material is subject to degradation. Because antisense interference requires that the interfering material accumulate at a relatively high concentration (at or above the concentration of endogenous mRNA), the amount required to be delivered is a major constraint on efficacy. As a consequence, much of the effort in developing antisense technology has been focused on the production of modified nucleic acids that are both stable to nuclease digestion and able to diffuse readily into cells. The use of antisense interference for gene therapy or other whole-organism applications has been limited by the large amounts of oligonucleotide that need to be synthesized from non-natural analogs, the cost of such synthesis, and the difficulty even with high doses of maintaining a sufficiently concentrated and uniform pool of interfering material in each cell.

Triple-Helix Approaches to Engineer Interference

A second, proposed method for engineered interference is based on a triple helical nucleic acid structure. This approach relies on the rare ability of certain nucleic acid populations to adopt a triple-stranded structure. Under physiological conditions, nucleic acids are virtually all single- or double-stranded, and rarely if ever form triple-stranded structures. It has been known for some time, however, that certain simple purine- or pyrimidine-rich sequences could form a triple-stranded molecule in vitro under extreme conditions of pH (i.e., in a test tube). Such structures are generally very transient under physiological conditions, so that simple delivery of unmodified nucleic acids designed to produce triple-strand structures does not yield interference. As with antisense, development of triple-strand technology for use in vivo has focused on the development of modified nucleic acids that would be more stable and more readily absorbed by cells in vivo. An additional goal in developing this technology has been to produce modified nucleic acids for which the formation of triple-stranded material proceeds effectively at physiological pH.

Co-Suppression Phenomena and Their Use in Genetic Engineering

A third approach to gene-specific interference is a set of operational procedures grouped under the name "co-suppression". This approach was first described in plants and refers to the ability of transgenes to cause silencing of an unlinked but homologous gene. More recently, phenomena similar to co-suppression have been reported in two animals: *C. elegans* and *Drosophila*. Co-suppression was first observed by accident, with reports coming from groups using transgenes in attempts to achieve over-expression of a potentially useful locus. In some cases the over-expression was successful while, in many others, the result was opposite from that expected. In those cases, the transgenic plants actually showed less expression of the endogenous gene. Several mechanisms have so far been proposed for transgene-mediated co-suppression in plants; all of these mechanistic proposals remain hypothetical, and no definitive mechanistic description of the process has been presented. The models that have been proposed to explain co-suppression can be placed in two different categories. In one set of proposals, a direct physical interaction at the DNA- or chromatin-level between two different chromosomal sites has been hypothesized to occur; an as-yet-unidentified mechanism would then lead to de novo methylation and subsequent suppression of gene expression. Alternatively, some have postulated an RNA intermediate, synthesized at the transgene locus, which might then act to produce interference with the endogenous gene. The characteristics of the interfering RNA, as well as the nature of the interference process, have not been determined. Recently, a set of experiments with RNA viruses have provided some support for the possibility of RNA intermediates in the interference process. In these experiments, a replicating RNA virus is modified to include a segment from a gene of interest. This modified virus is then tested for its ability to interfere with expression of the endogenous gene. Initial results with this technique have been encouraging, however, the properties of the viral RNA that are responsible for interference effects have not been determined and, in any case, would be limited to plants which are hosts of the plant virus.

Distinction Between the Present Invention and Antisense Approaches

The present invention differs from antisense-mediated interference in both approach and effectiveness. Antisense-mediated genetic interference methods have a major challenge: delivery to the cell interior of specific single-stranded nucleic acid molecules at a concentration that is equal to or greater than the concentration of endogenous mRNA. Double-stranded RNA-mediated inhibition has advantages both in the stability of the material to be delivered and the concentration required for effective inhibition. Below, we disclose that in the model organism *C. elegans*, the present invention is at least 100-fold more effective than an equivalent antisense approach (i.e., dsRNA is at least 100-fold more effective than the injection of purified antisense RNA in reducing gene expression). These comparisons also demonstrate that inhibition by double-stranded RNA must occur by a mechanism distinct from antisense interference.

Distinction Between the Present Invention and Triple-Helix Approaches

The limited data on triple strand formation argues against the involvement of a stable triple-strand intermediate in the present invention. Triple-strand structures occur rarely, if at all, under physiological conditions and are limited to very unusual base sequence with long runs of purines and pyrimidines. By contrast, dsRNA-mediated inhibition occurs efficiently under physiological conditions, and occurs with a wide variety of inhibitory and target nucleotide sequences. The present invention has been used to inhibit expression of 18 different genes, providing phenocopies of null mutations in these genes of known function. The extreme environmental and sequence constraints on triple-helix formation make it unlikely that dsRNA-mediated inhibition in *C. elegans* is mediated by a triple-strand structure.

Distinction Between Present Invention and Co-Suppression Approaches

The transgene-mediated genetic interference phenomenon called co-suppression may include a wide variety of different processes. From the viewpoint of application to other types of organisms, the co-suppression phenomenon in plants is difficult to extend. A confounding aspect in creating a general technique based on co-suppression is that some transgenes in plants lead to suppression of the endogenous locus and some do not. Results in *C. elegans* and *Drosophila* indicate that certain transgenes can cause interference (i.e., a quantitative decrease in the activity of the corresponding endogenous locus) but that most transgenes do not produce such an effect. The lack of a predictable effect in plants, nematodes, and insects greatly limits the usefulness of simply adding transgenes to the genome to interfere with gene expression. Viral-mediated co-suppression in plants appears to be quite effective, but has a number of drawbacks. First, it is not clear what aspects of the viral structure are critical for the observed interference. Extension to another system would require discovery of a virus in that system which would have these properties, and such a library of useful viral agents are not available for many organisms. Second, the use of a replicating virus within an organism to effect genetic changes (e.g., long- or short-term gene therapy) requires considerably more monitoring and oversight for deleterious effects than the use of a defined nucleic acid as in the present invention.

The present invention avoids the disadvantages of the previously-described methods for genetic interference. Several advantages of the present invention are discussed below, but numerous others will be apparent to one of ordinary skill in the biotechnology and genetic engineering arts.

SUMMARY OF THE INVENTION

A process is provided for inhibiting expression of a target gene in a cell. The process comprises introduction of RNA with partial or fully double-stranded character into the cell or into the extracellular environment. Inhibition is specific in that a nucleotide sequence from a portion of the target gene is chosen to produce inhibitory RNA. We disclose that this process is (1) effective in producing inhibition of gene expression, (2) specific to the targeted gene, and (3) general in allowing inhibition of many different types of target gene.

The target gene may be a gene derived from the cell, an endogenous gene, a transgene, or a gene of a pathogen which is present in the cell after infection thereof. Depending on the particular target gene and the dose of double stranded RNA material delivered, the procedure may provide partial or complete loss of function for the target gene. A reduction or loss of gene expression in at least 99% of targeted cells has been shown. Lower doses of injected material and longer times after administration of dsRNA may result in inhibition in a smaller fraction of cells. Quantitation of gene expression in a cell may show similar amounts of inhibition at the level of accumulation of target mRNA or translation of target protein.

The RNA may comprise one or more strands of polymerized ribonucleotide; it may include modifications to either the phosphate-sugar backbone or the nucleoside. The double-stranded structure may be formed by a single self-complementary RNA strand or two complementary RNA strands. RNA duplex formation may be initiated either inside or outside the cell. The RNA may be introduced in an amount which allows delivery of at least one copy per cell. Higher doses of double-stranded material may yield more effective inhibition. Inhibition is sequence-specific in that nucleotide sequences corresponding to the duplex region of the RNA are targeted for genetic inhibition. RNA containing a nucleotide sequences identical to a portion of the target gene is preferred for inhibition. RNA sequences with insertions, deletions, and single point mutations relative to the target sequence have also been found to be effective for inhibition. Thus, sequence identity may optimized by alignment algorithms known in the art and calculating the percent difference between the nucleotide sequences. Alternatively, the duplex region of the RNA may be defined functionally as a nucleotide sequence that is capable of hybridizing with a portion of the target gene transcript.

The cell with the target gene may be derived from or contained in any organism (e.g., plant, animal, protozoan, virus, bacterium, or fungus). RNA may be synthesized either in vivo or in vitro. Endogenous RNA polymerase of the cell may mediate transcription in vivo, or cloned RNA polymerase can be used for transcription in vivo or in vitro. For transcription from a transgene in vivo or an expression construct, a regulatory region may be used to transcribe the RNA strand (or strands).

The RNA may be directly introduced into the cell (i.e., intracellularly); or introduced extracellularly into a cavity, interstitial space, into the circulation of an organism, introduced orally, or may be introduced by bathing an organism in a solution containing RNA. Methods for oral introduction include direct mixing of RNA with food of the organism, as well as engineered approaches in which a species that is used as food is engineered to express an RNA, then fed to the organism to be affected. Physical methods of introducing nucleic acids include injection directly into the cell or extracellular injection into the organism of an RNA solution.

The advantages of the present invention include: the ease of introducing double-stranded RNA into cells, the low concentration of RNA which can be used, the stability of double-stranded RNA, and the effectiveness of the inhibition. The ability to use a low concentration of a naturally-occurring nucleic acid avoids several disadvantages of anti-sense interference. This invention is not limited to in vitro use or to specific sequence compositions, as are techniques based on triple-strand formation. And unlike antisense interference, triple-strand interference, and co-suppression, this invention does not suffer from being limited to a particular set of target genes, a particular portion of the target gene's nucleotide sequence, or a particular transgene or viral delivery method. These concerns have been a serious obstacle to designing general strategies according to the prior art for inhibiting gene expression of a target gene of interest.

Furthermore, genetic manipulation becomes possible in organisms that are not classical genetic models. Breeding and screening programs may be accelerated by the ability to rapidly assay the consequences of a specific, targeted gene disruption. Gene disruptions may be used to discover the function of the target gene, to produce disease models in which the target gene are involved in causing or preventing a pathological condition, and to produce organisms with improved economic properties.

BRIEF DESCRIPTION OF THE DRAWINGS

FIGS. 2 A-I show analysis of inhibitory RNA effects in individual cells. These experiments were carried out in a reporter strain (called PD4251) expressing two different reporter proteins, nuclear GFP-LacZ and mitochondrial GFP. The micrographs show progeny of injected animals visualized by a fluorescence microscope. Panels A (young larva), B (adult), and C (adult body wall; high magnification) result from injection of a control RNA (ds-unc22A). Panels D-F show progeny of animals injected with ds-gfpG. Panels G-J demonstrate specificity. Animals are injected with ds-lacZL RNA, which should affect the nuclear but not the mitochondrial reporter construct. Panel H shows a typical adult, with nuclear GFP-LacZ lacking in almost all body-wall muscles but retained in vulval muscles. Scale bars are 20 μm.

FIGS. 5 A-C show examples of genetic inhibition following ingestion by *C. elegans* of dsRNAs from expressing bacteria. Panel A: General strategy for production of dsRNA by cloning a segment of interest between flanking copies of the bacteriophage T7 promoter and transcribing both strands of the segment by transfecting a bacterial strain (BL21/DE3)[28] expressing the T7 polymerase gene from an inducible (Lac) promoter. Panel B: A GFP-expressing *C. elegans* strain, PD4251 (see FIG. 2), fed on a native bacterial host. Panel C: PD4251 animals reared on a diet of bacteria expressing dsRNA corresponding to the coding region for gfp.

DETAILED DESCRIPTION OF THE INVENTION

Figure 1:
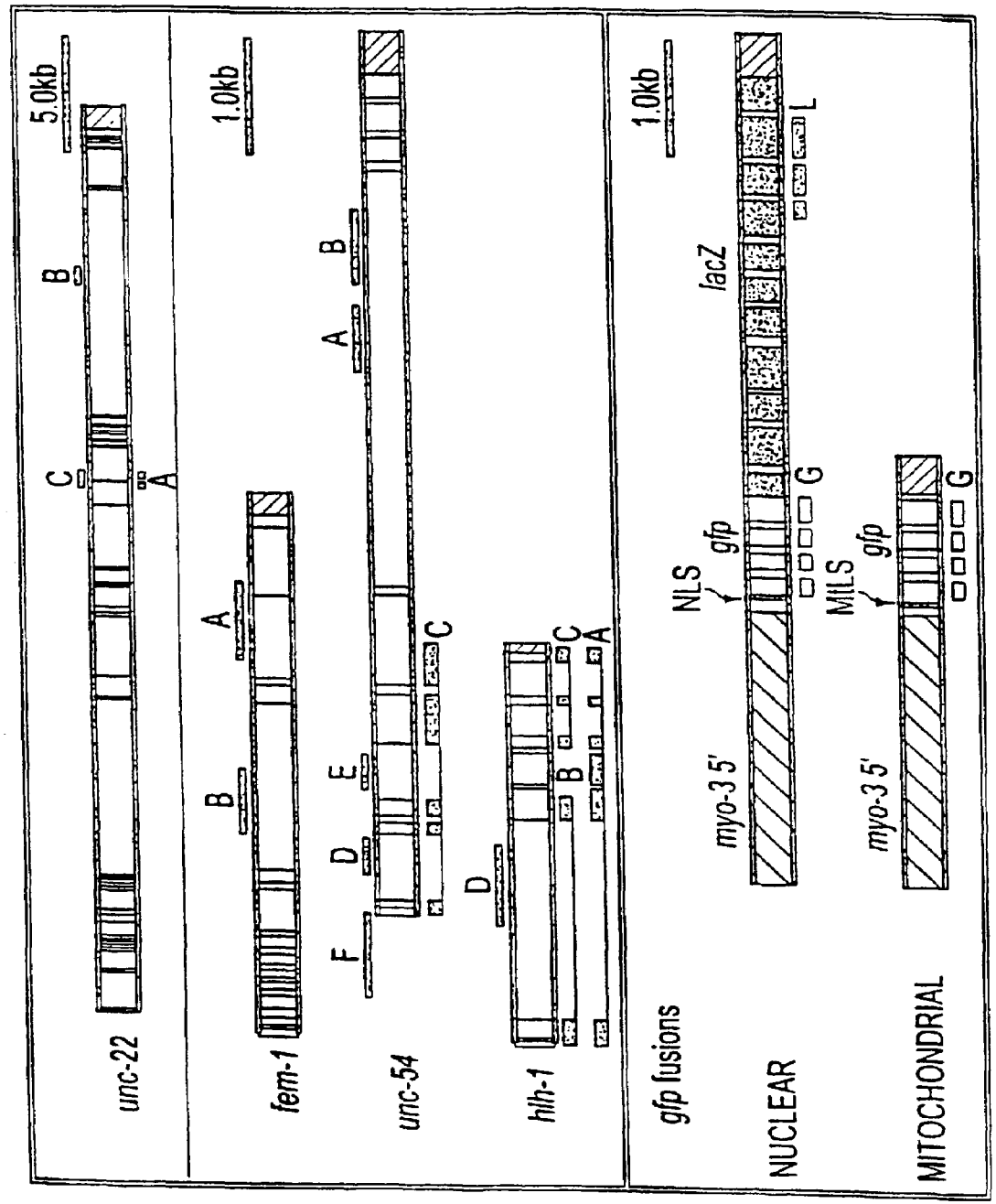
FIG. 1 shows the genes used to study RNA-mediated genetic inhibition in *C. elegans*. Intron-exon structure for genes used to test RNA-mediated inhibition are shown (exons: filled boxes; introns: open boxes; 5' and 3' untranslated regions: shaded; unc-22[9], unc-54[12], fem-1[14], and hlh-1[15]).
Figure 3A:
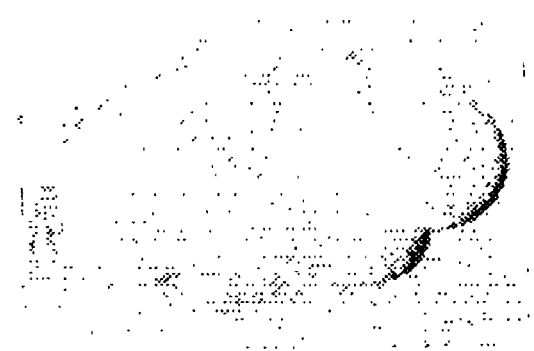
FIGS. 3 A-D show effects of double-stranded RNA corresponding to mex-3 on levels of the endogenous mRNA. Micrographs show in situ hybridization to embryos (dark stain). Panel A: Negative control showing lack of staining in the absence of hybridization probe. Panel B: Embryo from uninjected parent (normal pattern of endogenous mex-3 RNA[20]). Panel C: Embryo from a parent injected with purified mex-3B antisense RNA. These embryos and the parent animals retain the mex-3 mRNA, although levels may have been somewhat less than wild type. Panel D: Embryo from a parent injected with dsRNA corresponding to mex-3B; no mex-3 RNA was detected. Scale: each embryo is approximately 50 μm in length.
Figure 3B:
Figure 3C:
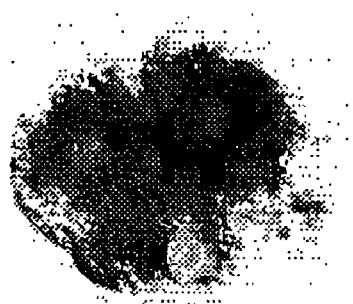
Figure 3D:

The present invention provides a method of producing sequence-specific inhibition of gene expression by introducing double-stranded RNA (dsRNA). A process is provided for inhibiting expression of a target gene in a cell. The process comprises introduction of RNA with partial or fully double-stranded character into the cell. Inhibition is sequence-specific in that a nucleotide sequence from a portion of the target gene is chosen to produce inhibitory RNA. We disclose that this process is (1) effective in producing inhibition of gene expression, (2) specific to the targeted gene, and (3) general in allowing inhibition of many different types of target gene.

The target gene may be a gene derived from the cell (i.e., a cellular gene), an endogenous gene (i.e., a cellular gene present in the genome), a transgene (i.e., a gene construct inserted at an ectopic site in the genome of the cell), or a gene from a pathogen which is capable of infecting an organism from which the cell is derived. Depending on the particular target gene and the dose of double stranded RNA material delivered, this process may provide partial or complete loss of function for the target gene. A reduction or loss of gene expression in at least 99% of targeted cells has been shown.

Inhibition of gene expression refers to the absence (or observable decrease) in the level of protein and/or mRNA product from a target gene. Specificity refers to the ability to inhibit the target gene without manifest effects on other genes of the cell. The consequences of inhibition can be confirmed by examination of the outward properties of the cell or organism (as presented below in the examples) or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS). For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracyclin.

Depending on the assay, quantitation of the amount of gene expression allows one to determine a degree of inhibition which is greater than 10%, 33%, 50%, 90%, 95% or 99% as compared to a cell not treated according to the present invention. Lower doses of injected material and longer times after administration of dsRNA may result in inhibition in a smaller fraction of cells (e.g., at least 10%, 20%, 50%, 75%, 90%, or 95% of targeted cells). Quantitation of gene expression in a cell may show similar amounts of inhibition at the level of accumulation of target mRNA or translation of target protein. As an example, the efficiency of inhibition may be determined by assessing the amount of gene product in the cell: mRNA may be detected with a hybridization probe having a nucleotide sequence outside the region used for the inhibitory double-stranded RNA, or translated polypeptide may be detected with an antibody raised against the polypeptide sequence of that region.

The RNA may comprise one or more strands of polymerized ribonucleotide. It may include modifications to either the phosphate-sugar backbone or the nucleoside. For example, the phosphodiester linkages of natural RNA may be modified to include at least one of a nitrogen or sulfur heteroatom. Modifications in RNA structure may be tailored to allow specific genetic inhibition while avoiding a general panic response in some organisms which is generated by dsRNA. Likewise, bases may be modified to block the activity of adenosine deaminase. RNA may be produced enzymatically or by partial/total organic synthesis, any modified ribonucleotide can be introduced by in vitro enzymatic or organic synthesis.

The double-stranded structure may be formed by a single self-complementary RNA strand or two complementary RNA strands. RNA duplex formation may be initiated either inside or outside the cell. The RNA may be introduced in an amount which allows delivery of at least one copy per cell. Higher doses (e.g., at least 5, 10, 100, 500 or 1000 copies per cell) of double-stranded material may yield more effective inhibition; lower doses may also be useful for specific applications. Inhibition is sequence-specific in that nucleotide sequences corresponding to the duplex region of the RNA are targeted for genetic inhibition.

RNA containing a nucleotide sequences identical to a portion of the target gene are preferred for inhibition. RNA sequences with insertions, deletions, and single point mutations relative to the target sequence have also been found to be effective for inhibition. Thus, sequence identity may optimized by sequence comparison and alignment algorithms known in the art (see Gribskov and Devereux, *Sequence Analysis Primer*, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing). The length of the identical nucleotide sequences may be at least 25, 50, 100, 200, 300 or 400 bases.

As disclosed herein, 100% sequence identity between the RNA and the target gene is not required to practice the present invention. Thus the invention has the advantage of being able to tolerate sequence variations that might be expected due to genetic mutation, strain polymorphism, or evolutionary divergence.

The cell with the target gene may be derived from or contained in any organism. The organism may a plant, animal, protozoan, bacterium, virus, or fungus. The plant may be a monocot, dicot or gymnosperm; the animal may be a vertebrate or invertebrate. Preferred microbes are those used in agriculture or by industry, and those that are pathogenic for plants or animals. Fungi include organisms in both the mold and yeast morphologies.

Plants include arabidopsis; field crops (e.g., alfalfa, barley, bean, corn, cotton, flax, pea, rape, rice, rye, safflower, sorghum, soybean, sunflower, tobacco, and wheat); vegetable crops (e.g., asparagus, beet, broccoli, cabbage, carrot, cauliflower, celery, cucumber, eggplant, lettuce, onion, pepper, potato, pumpkin, radish, spinach, squash, taro, tomato, and zucchini); fruit and nut crops (e.g., almond, apple, apricot, banana, blackberry, blueberry, cacao, cherry, coconut, cranberry, date, fajoa, filbert, grape, grapefruit, guava, kiwi, lemon, lime, mango, melon, nectarine, orange, papaya, passion fruit, peach, peanut, pear, pineapple, pistachio, plum, raspberry, strawberry, tangerine, walnut, and watermelon); and ornamentals (e.g., alder, ash, aspen, azalea, birch, boxwood, camellia, carnation, chrysanthemum, elm, fir, ivy, jasmine, juniper, oak, palm, poplar, pine, redwood, rhododendron, rose, and rubber).

Examples of vertebrate animals include fish, mammal, cattle, goat, pig, sheep, rodent, hamster, mouse, rat, primate, and human; invertebrate animals include nematodes, other worms, drosophila, and other insects. Representative generae of nematodes include those that infect animals (e.g., Ancylostoma, Ascaridia, Ascaris, Bunostomum, Caenorhabditis, Capillaria, Chabertia, Cooperia, Dictyocaulus, Haemonchus, Heterakis, Nematodirus, Oesophagostomum, Ostertagia, Oxyuris, Parascaris, Strongylus, Toxascaris, Trichuris, Trichostrongylus, Tfhchonema, Toxocara, Uncinaria) and those that infect plants (e.g., Bursaphalenchus, Criconemella, Diiylenchus, Ditylenchus, Globodera, Helicotylenchus, Heterodera, Longidorus, Melodoigyne, Nacobbus, Paratylenchus, Pratylenchus, Radopholus, Rotelynchus, Tylenchus, and Xiphinema). Representative orders of insects include Coleoptera, Diptera, Lepidoptera, and Homoptera.

The cell having the target gene may be from the germ line or somatic, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine or exocrine glands.

RNA may be synthesized either in vivo or in vitro. Endogenous RNA polymerase of the cell may mediate transcription in vivo, or cloned RNA polymerase can be used for transcription in vivo or in vitro. For transcription from a transgene in vivo or an expression construct, a regulatory region (e.g., promoter, enhancer, silencer, splice donor and acceptor, polyadenylation) may be used to transcribe the RNA strand (or strands). Inhibition may be targeted by specific transcription in an organ, tissue, or cell type; stimulation of an environmental condition (e.g., infection, stress, temperature, chemical inducers); and/or engineering transcription at a developmental stage or age. The RNA strands may or may not be polyadenylated; the RNA strands may or may not be capable of being translated into a polypeptide by a cell's translational apparatus. RNA may be chemically or enzymatically synthesized by manual or automated reactions. The RNA may be synthesized by a cellular RNA polymerase or a bacteriophage RNA polymerase (e.g., T3, T7, SP6). The use and production of an expression construct are known in the art[32, 33, 34] (see also WO 97/32016; U.S. Pat. Nos. 5,593,874, 5,698,425, 5,712,135, 5,789,214, and 5,804,693; and the references cited therein). If synthesized chemically or by in vitro enzymatic synthesis, the RNA may be purified prior to introduction into the cell. For example, RNA can be purified from a mixture by extraction with a solvent or resin, precipitation, electrophoresis, chromatography, or a combination thereof. Alternatively, the RNA may be used with no or a minimum of purification to avoid losses due to sample processing. The RNA may be dried for storage or dissolved in an aqueous solution. The solution may contain buffers or salts to promote annealing, and/or stabilization of the duplex strands.

RNA may be directly introduced into the cell (i.e., intracellularly); or introduced extracellularly into a cavity, interstitial space, into the circulation of an organism, introduced orally, or may be introduced by bathing an organism in a solution containing the RNA. Methods for oral introduction include direct mixing of the RNA with food of the organism, as well as engineered approaches in which a species that is used as food is engineered to express the RNA, then fed to the organism to be affected. For example, the RNA may be sprayed onto a plant or a plant may be genetically engineered to express the RNA in an amount sufficient to kill some or all of a pathogen known to infect the plant. Physical methods of introducing nucleic acids, for example, injection directly into the cell or extracellular injection into the organism, may also be used. We disclose herein that in C. elegans, double-stranded RNA introduced outside the cell inhibits gene expression. Vascular or extravascular circulation, the blood or lymph system, the phloem, the roots, and the cerebrospinal fluid are sites where the RNA may be introduced. A transgenic organism that expresses RNA from a recombinant construct may be produced by introducing the construct into a zygote, an embryonic stem cell, or another multipotent cell derived from the appropriate organism.

Physical methods of introducing nucleic acids include injection of a solution containing the RNA, bombardment by particles covered by the RNA, soaking the cell or organism in a solution of the RNA, or electroporation of cell membranes in the presence of the RNA. A viral construct packaged into a viral particle would accomplish both efficient introduction of an expression construct into the cell and transcription of RNA encoded by the expression construct. Other methods known in the art for introducing nucleic acids to cells may be used, such as lipid-mediated carrier transport, chemical-mediated transport, such as calcium phosphate, and the like. Thus the RNA may be introduced along with components that perform one or more of the following activities: enhance RNA uptake by the cell, promote annealing of the duplex strands, stabilize the annealed strands, or other-wise increase inhibition of the target gene.

The present invention may be used to introduce RNA into a cell for the treatment or prevention of disease. For example, dsRNA may be introduced into a cancerous cell or tumor and thereby inhibit gene expression of a gene required for maintenance of the carcinogenic/tumorigenic phenotype. To prevent a disease or other pathology, a target gene may be selected which is required for initiation or maintenance of the disease/pathology.

Treatment would include amelioration of any symptom associated with the disease or clinical indication associated with the pathology.

A gene derived from any pathogen may be targeted for inhibition. For example, the gene could cause immunosuppression of the host directly or be essential for replication of the pathogen, transmission of the pathogen, or maintenance of the infection.

The inhibitory RNA could be introduced in cells in vitro or ex vivo and then subsequently placed into an animal to affect therapy, or directly treated by in vivo administration. A method of gene therapy can be envisioned. For example, cells at risk for infection by a pathogen or already infected cells, particularly human immunodeficiency virus (HIV) infections, may be targeted for treatment by introduction of RNA according to the invention. The target gene might be a pathogen or host gene responsible for entry of a pathogen into its host, drug metabolism by the pathogen or host, replication or integration of the pathogen's genome, establishment or spread of an infection in the host, or assembly, of the next generation of pathogen. Methods of prophylaxis (i.e., prevention or decreased risk of infection), as well as reduction in the frequency or severity of symptoms associated with infection, can be envisioned.

The present invention could be used for treatment or development of treatments for cancers of any type, including solid tumors and leukemias, including: apudoma, choristoma, branchioma, malignant carcinoid syndrome, carcinoid heart disease, carcinoma (e.g., Walker, basal cell, basosquamous, Brown-Pearce, ductal, Ehrlich tumor, in situ, Krebs 2, Merkel cell, mucinous, non-small cell lung, oat cell, papillary, scirrhous, bronchiolar, bronchogenic, squamous cell, and transitional cell), histiocytic disorders, leukemia (e.g., B cell, mixed cell, null cell, T cell, T-cell chronic, HTLV-II-associated, lymphocytic acute, lymphocytic chronic, mast cell, and myeloid), histiocytosis malignant, Hodgkin disease, immunoproliferative small, non-Hodgkin lymphoma, plasmacytoma, reticuloendotheliosis, melanoma, chondroblastoma, chondroma, chondrosarcoma, fibroma, fibrosarcoma, giant cell tumors, histiocytoma, lipoma, liposarcoma, mesothelioma, myxoma, myxosarcoma, osteoma, osteosarcoma, Ewing sarcoma, synovioma, adenofibroma, adenolymphoma, carcinosarcoma, chordoma, cranio-pharyngioma, dysgerminoma, hamartoma, mesenchymoma, mesonephroma, myosarcoma, ameloblastoma, cementoma, odontoma, teratoma, thymoma, trophoblastic tumor, adenocarcinoma, adenoma, cholangioma, cholesteatoma, cylindroma, cystadenocarcinoma, cystadenoma, granulosa cell tumor, gynandroblastoma, hepatoma, hidradenoma, islet cell tumor, Leydig cell tumor, papilloma, Sertoli cell tumor, theca cell tumor, leiomyoma, leiomyosarcoma, myoblastoma, myoma, myosarcoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, paraganglioma nonchromaffin, angiokeratoma, angiolymphoid hyperplasia with eosinophilia, angioma sclerosing, angiomatosis, glomangioma, hemangioendothelioma, hemangioma, hemangiopericytoma, hemangiosarcoma, lymphangioma, lymphangiomyoma, lymphangiosarcoma, pinealoma, carcinosarcoma, chondrosarcoma, cystosarcoma phyllodes, fibrosarcoma, hemangiosarcoma, leiomyosarcoma, leukosarcoma, liposarcoma, lymphangiosarcoma, myosarcoma, myxosarcoma, ovarian carcinoma, rhabdomyosarcoma, sarcoma (e.g., Ewing, experimental, Kaposi, and mast cell), neoplasms (e.g., bone, breast, digestive system, colorectal, liver, pancreatic, pituitary, testicular, orbital, head and neck, central nervous system, acoustic, pelvic, respiratory tract, and urogenital), neurofibromatosis, and cervical dysplasia, and for treatment of other conditions in which cells have become immortalized or transformed. The invention could be used in combination with other treatment modalities, such as chemotherapy, cryotherapy, hyperthermia, radiation therapy, and the like.

As disclosed herein, the present invention may is not limited to any type of target gene or nucleotide sequence. But the following classes of possible target genes are listed for illustrative purposes: developmental genes (e.g., adhesion molecules, cyclin kinase inhibitors, Wnt family members, Pax family members, Winged helix family members, Hox family members, cytokines/lymphokines and their receptors, growth/differentiation factors and their receptors, neurotransmitters and their receptors); oncogenes (e.g., ABL1, BCL1, BCL2, BCL6, CBFA2, CBL, CSF1R, ERBA, ERBB, EBRB2, ETS1, ETS1, ETV6, FGR, FOS, FYN, HCR, HRAS, JUN, KRAS, LCK, LYN, MDM2, MLL, MYB, MYC, MYCL1, MYCN, NRAS, PIM1, PML, RET, SRC, TAL1, TCL3, and YES); tumor suppressor genes (e.g., APC, BRCA1, BRCA2, MADH4, MCC, NF1, NF2, RB1, TP53, and WT1); and enzymes (e.g., ACC synthases and oxidases, ACP desaturases and hydroxylases, ADP-glucose pyrophorylases, ATPases, alcohol dehydrogenases, amylases, amyloglucosidases, catalases, cellulases, chalcone synthases, chitinases, cyclooxygenases, decarboxylases, dextrinases, DNA and RNA polymerases, galactosidases, glucanases, glucose oxidases, granule-bound starch synthases, GTPases, helicases, hemicellulases, integrases, inulinases, invertases, isomerases, kinases, lactases, lipases, lipoxygenases, lysozymes, nopaline synthases, octopine synthases, pectinesterases, peroxidases, phosphatases, phospholipases, phosphorylases, phytases, plant growth regulator synthases, polygalacturonases, proteinases and peptidases, pullanases, recombinases, reverse transcriptases, RUBISCOs, topoisomerases, and xylanases).

The present invention could comprise a method for producing plants with reduced susceptibility to climatic injury, susceptibility to insect damage, susceptibility to infection by a pathogen, or altered fruit ripening characteristics. The targeted gene may be an enzyme, a plant structural protein, a gene involved in pathogenesis, or an enzyme that is involved in the production of a non-proteinaceous part of the plant (i.e., a carbohydrate or lipid). If an expression construct is used to transcribe the RNA in a plant, transcription by a wound- or stress-inducible; tissue-specific (e.g., fruit, seed, anther, flower, leaf, root); or otherwise regulatable (e.g., infection, light, temperature, chemical) promoter may be used. By inhibiting enzymes at one or more points in a metabolic pathway or genes involved in pathogenesis, the effect may be enhanced: each activity will be affected and the effects may be magnified by targeting multiple different components. Metabolism may also be manipulated by inhibiting feedback control in the pathway or production of unwanted metabolic byproducts.

The present invention may be used to reduce crop destruction by other plant pathogens such as arachnids, insects, nematodes, protozoans, bacteria, or fungi. Some such plants and their pathogens are listed in *Index of Plant Diseases in the United States* (U.S. Dept. of Agriculture Handbook No. 165, 1960); *Distribution of Plant-Parasitic Nematode Species in North America* (Society of Nematologists, 1985); and *Fungi on Plants and Plant Products in the United States* (American Phytopathological Society, 1989). Insects with reduced ability to damage crops or improved ability to prevent other destructive insects from damaging crops may be produced. Furthermore, some nematodes are vectors of plant pathogens, and may be attacked by other beneficial nematodes which have no effect on plants. Inhibition of target gene activity could be used to delay or prevent entry into a particular developmental step (e.g., metamorphosis), if plant disease was associated with a particular stage of the pathogen's life cycle. Interactions between pathogens may also be modified by the invention to limit crop damage. For example, the ability of beneficial nematodes to attack their harmful prey may be enhanced by inhibition of behavior-controlling nematode genes according to the invention.

Although pathogens cause disease, some of the microbes interact with their plant host in a beneficial manner. For example, some bacteria are involved in symbiotic relationships that fix nitrogen and some fungi produce phytohormones. Such beneficial interactions may be promoted by using the present invention to inhibit target gene activity in the plant and/or the microbe.

Another utility of the present invention could be a method of identifying gene function in an organism comprising the use of double-stranded RNA to inhibit the activity of a target gene of previously unknown function. Instead of the time consuming and laborious isolation of mutants by traditional genetic screening, functional genomics would envision determining the function of uncharacterized genes by employing the invention to reduce the amount and/or alter the timing of target gene activity. The invention could be used in determining potential targets for pharmaceutics, understanding normal and pathological events associated with development, determining signaling pathways responsible for postnatal development/aging, and the like. The increasing speed of acquiring nucleotide sequence information from genomic and expressed gene sources, including total sequences for the yeast, *D. melanogaster*, and *C. elegans* genomes, can be coupled with the invention to determine gene function in an organism (e.g., nematode). The preference of different organisms to use particular codons, searching sequence databases for related gene products, correlating the linkage map of genetic traits with the physical map from which the nucleotide sequences are derived, and artificial intelligence methods may be used to define putative open reading frames from the nuicleotide sequences acquired in such sequencing projects.

A simple assay would be to inhibit gene expression according to the partial sequence available from an expressed sequence tag (EST). Functional alterations in growth, development, metabolism, disease resistance, or other biological processes would be indicative of the normal role of the EST's gene product.

The ease with which RNA can be introduced into an intact cell/organism containing the target gene allows the present invention to be used in high throughput screening (HTS). For example, duplex RNA can be produced by an amplification reaction using primers flanking the inserts of any gene library derived from the target cell/organism. Inserts may be derived from genomic DNA or mRNA (e.g., cDNA and cRNA). Individual clones from the library can be replicated and then isolated in separate reactions, but preferably the library is maintained in individual reaction vessels (e.g., a 96-well microtiter plate) to minimize the number of steps required to practice the invention and to allow automation of the process. Solutions containing duplex RNAs that are capable of inhibiting the different expressed genes can be placed into individual wells positioned on a microtiter plate as an ordered array, and intact cells/organisms in each well can be assayed for any changes or modifications in behavior or development due to inhibition of target gene activity. The amplified RNA can be fed directly to, injected into, the cell/organism containing the target gene. Alternatively, the duplex RNA can be produced by in vivo or in vitro transcription from an expression construct used to produce the library. The construct can be replicated as individual clones of the library and transcribed to produce the RNA; each clone can then be fed to, or injected into, the cell/organism containing the target gene. The function of the target gene can be assayed from the effects it has on the cell/organism when gene activity is inhibited. This screening could be amenable to small subjects that can be processed in large number, for example: arabidopsis, bacteria, drosophila, fungi, nematodes, viruses, zebrafish, and tissue culture cells derived from mammals.

A nematode or other organism that produces a calorimetric, fluorogenic, or luminescent signal in response to a regulated promoter (e.g., transfected with a reporter gene construct) can be assayed in an HTS format to identify DNA-binding proteins that regulate the promoter. In the assay's simplest form, inhibition of a negative regulator results in an increase of the signal and inhibition of a positive regulator results in a decrease of the signal.

If a characteristic of an organism is determined to be genetically linked to a polymorphism through RFLP or QTL analysis, the present invention can be used to gain insight regarding whether that genetic polymorphism might be directly responsible for the characteristic. For example, a fragment defining the genetic polymorphism or sequences in the vicinity of such a genetic polymorphism can be amplified to produce an RNA, the duplex RNA can be introduced to the organism, and whether an alteration in the characteristic is correlated with inhibition can be determined. Of course, there may be trivial explanations for negative results with this type of assay, for example: inhibition of the target gene causes lethality, inhibition of the target gene may not result in any observable alteration, the fragment contains nucleotide sequences that are not capable of inhibiting the target gene, or the target gene's activity is redundant.

The present invention may be useful in allowing the inhibition of essential genes. Such genes may be required for cell or organism viability at only particular stages of development or cellular compartments. The functional equivalent of conditional mutations may be produced by inhibiting activity of the target gene when or where it is not required for viability. The invention allows addition of RNA at specific times of development and locations in the organism without introducing permanent mutations into the target genome.

If alternative splicing produced a family of transcripts that were distinguished by usage of characteristic exons, the present invention can target inhibition through the appropriate exons to specifically inhibit or to distinguish among the functions of family members. For example, a hormone that contained an alternatively spliced transmembrane domain may be expressed in both membrane bound and secreted forms. Instead of isolating a nonsense mutation that terminates translation before the transmembrane domain, the functional consequences of having only secreted hormone can be determined according to the invention by targeting the exon containing the transmembrane domain and thereby inhibiting expression of membrane-bound hormone.

The present invention may be used alone or as a component of a kit having at least one of the reagents necessary to carry out the in vitro or in vivo introduction of RNA to test samples or subjects. Preferred components are the dsRNA and a vehicle that promotes introduction of the dsRNA. Such a kit may also include instructions to allow a user of the kit to practice the invention.

Pesticides may include the RNA molecule itself, an expression construct capable of expressing the RNA, or organisms transfected with the expression construct. The pesticide of the present invention may serve as an arachnicide, insecticide, nematicide, viricide, bactericide, and/or fungicide. For example, plant parts that are accessible above ground (e.g., flowers, fruits, buds, leaves, seeds, shoots, bark, stems) may be sprayed with pesticide, the soil may be soaked with pesticide to access plant parts growing beneath ground level, or the pest may be contacted with pesticide directly. If pests interact with each other, the RNA may be transmitted between them. Alternatively, if inhibition of the target gene results in a beneficial effect on plant growth or development, the aforementioned RNA, expression construct, or transfected organism may be considered a nutritional agent. In either case, genetic engineering of the plant is not required to achieve the objectives of the invention.

Alternatively, an organism may be engineered to produce dsRNA which produces commercially or medically beneficial results, for example, resistance to a pathogen or its pathogenic effects, improved growth, or novel developmental patterns.

Used as either an pesticide or nutrient, a formulation of the present invention may be delivered to the end user in dry or liquid form: for example, as a dust, granulate, emulsion, paste, solution, concentrate, suspension, or encapsulation. Instructions for safe and effective use may also be provided with the formulation. The formulation might be used directly, but concentrates would require dilution by mixing with an extender provided by the formulator or the end user. Similarly, an emulsion, paste, or suspension may require the end user to perform certain preparation steps before application. The formulation may include a combination of chemical additives known in the art such as solid carriers, minerals, solvents, dispersants, surfactants, emulsifiers, tackifiers, binders, and other adjuvants. Preservatives and stabilizers may also be added to the formulation to facilitate storage. The crop area or plant may also be treated simultaneously or separately with other pesticides or fertilizers. Methods of application include dusting, scattering or pouring, soaking, spraying, atomizing, and coating. The precise physical form and chemical composition of the formulation, and its method of application, would be chosen to promote the objectives of the invention and in accordance with prevailing circumstances. Expression constructs and transfected hosts capable of replication may also promote the persistence and/or spread of the formulation.

Description of the dsRNA Inhibition Phenomenon in *C. elegans*

The operation of the present invention was shown in the model genetic organism *Caenorhabditis elegans*.

Introduction of RNA into cells had been seen in certain biological systems to interfere with function of an endogenous gene[1,2]. Many such effects were believed to result from a simple antisense mechanism dependent on hybridization between injected single-stranded RNA and endogenous transcripts. In other cases, a more complex mechanism had been suggested. One instance of an RNA-mediated mechanism was RNA interference (RNAi) phenomenon in the nematode *C. elegans*. RNAi had been used in a variety of studies to manipulate gene expression[3,4].

Despite the usefulness of RNAi in *C. elegans*, many features had been difficult to explain. Also, the lack of a clear understanding of the critical requirements for interfering RNA led to a sporadic record of failure and partial success in attempts to extend RNAi beyond the earliest stages following injection. A statement frequently made in the literature was that sense and antisense RNA preparations are each sufficient to cause interference The only precedent for such a situation was in plants where the process of co-suppression had a similar history of usefulness in certain cases, failure in others, and no ability to design interference protocols with a high chance of success. Working with *C. elegans*, we discovered an RNA structure that would give effective and uniform genetic inhibition. The prior art did not teach or suggest that RNA structure was a critical feature for inhibition of gene expression. Indeed the ability of crude sense and antisense preparations to produce interference[3,4] had been taken as an indication that RNA structure was not a critical factor. Instead, the extensive plant literature and much of the ongoing research in *C. elegans* was focused on the possibility that detailed features of the target gene sequence or its chromosomal locale was the critical feature for interfering with gene expression.

The inventors carefully purified sense or antisense RNA for unc-22 and tested each for gene-specific inhibition. While the crude sense and antisense preparations had strong interfering activity, it was found that the purified sense and antisense RNAs had only marginal inhibitory activity. This was unexpected because many techniques in molecular biology are based on the assumption that RNA produced with specific in vitro promoters (e.g., T3 or T7 RNA polymerase), or with characterized promoters in vivo, is produced predominantly from a single strand. The inventors had carried out purification of these crude preparations to investigate whether a small fraction of the RNA had an unusual structure which might be responsible for the observed genetic inhibition. To rigorously test whether double-stranded character might contribute to genetic inhibition, the inventors carried out additional purification of single-stranded RNAs and compared inhibitory activities of individual strands with that of the double-stranded hybrid.

The following examples are meant to be illustrative of the present invention; however, the practice of the invention is not limited or restricted in any way by them.

Analysis of RNA-Mediated Inhibition of *C. elegans* Genes

The unc-22 gene was chosen for initial comparisons of activity as a result of previous genetic analysis that yields a semi-quantitative comparison between unc-22 gene activity and the movement phenotypes of animals[3,8]: decreases in activity produce an increasingly severe twitching phenotype, while complete loss of function results in the additional appearance of muscle structural defects and impaired motility. unc-22 encodes an abundant but non-essential myofilament protein[7-9]. unc-22 mRNA is present at several thousand copies per striated muscle cell[3].

Figure 4A:
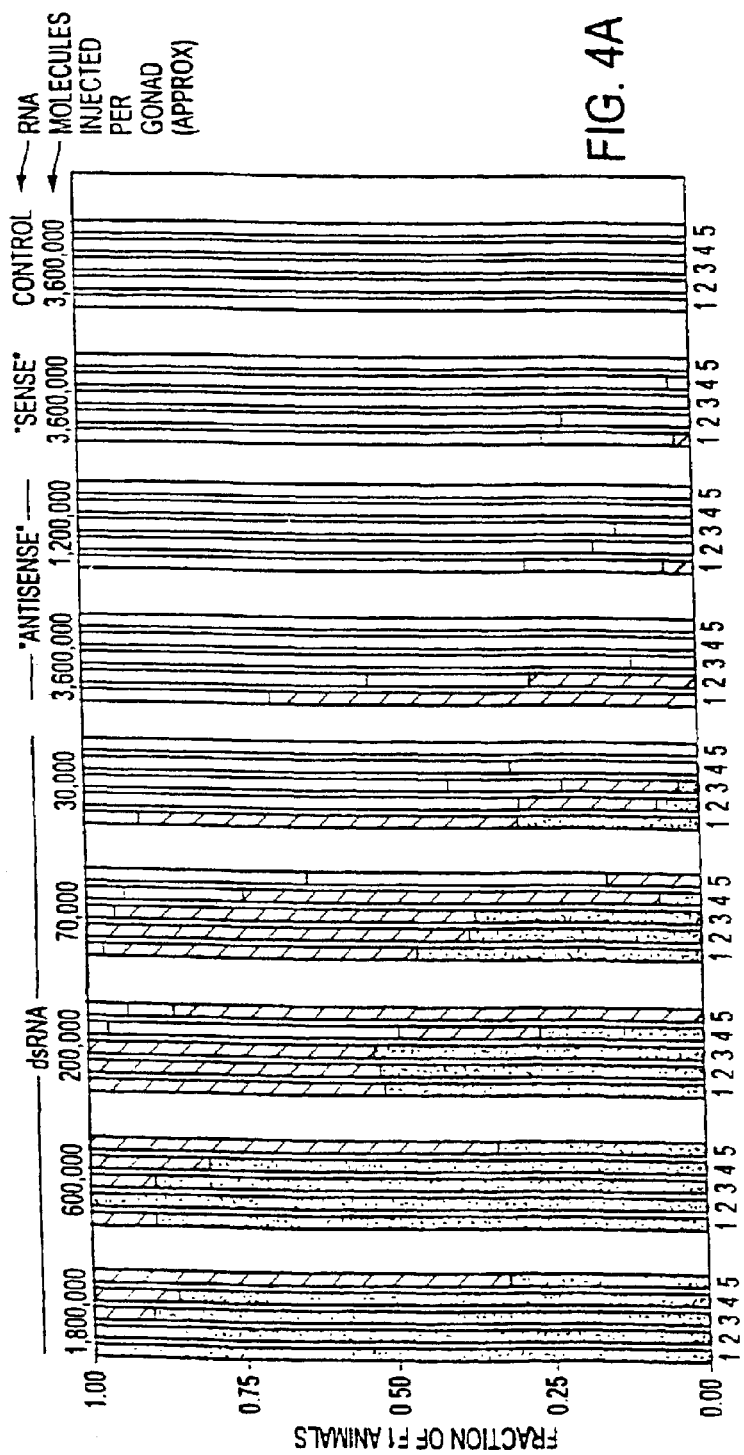
FIG. 4 shows inhibitory activity of unc-22A as a function of structure and concentration. The main graph indicates fractions in each behavioral class. Embryos in the uterus and already covered with an eggshell at the time of injection were not affected and, thus, are not included. Progeny cohort groups are labeled 1 for 0-6 hours, 2 for 6-15 hours, 3 for 15-27 hours, 4 for 27-41 hours, and 5 for 41-56 hours The bottom-left diagram shows genetically derived relationship between unc-22 gene dosage and behavior based on analyses of unc-22 heterozygotes and polyploids[8,3].
Figure 4B:
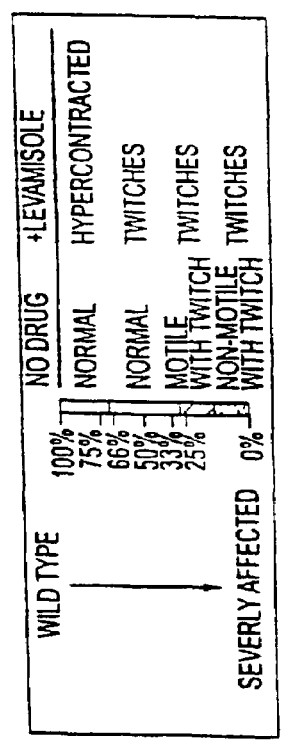

Purified antisense and sense RNAs covering a 742 nt segment of unc-22 had only marginal inhibitory activity, requiring a very high dose of injected RNA for any observable effect (FIG. 4). By contrast, a sense+antisense mixture produced a highly effective inhibition of endogenous gene activity (FIG. 4). The mixture was at least two orders of magnitude more effective than either single strand in inhibiting gene expression. The lowest dose of the sense+antisense mixture tested, approximately 60,000 molecules of each strand per adult, led to twitching phenotypes in an average of 100 progeny. unc-22 expression begins in embryos with approximately 500 cells. At this point, the original injected material would be diluted to at most a few molecules per cell.

The potent inhibitory activity of the sense+antisense mixture could reflect formation of double-stranded RNA (dsRNA), or conceivably some alternate synergy between the strands. Electrophoretic analysis indicated that the injected material was predominantly double stranded. The dsRNA was gel purified from the annealed mixture and found to retain potent inhibitory activity. Although annealing prior to injection was compatible with inhibition, it was not necessary. Mixing of sense and antisense RNAs in low salt (under conditions of minimal dsRNA formation), or rapid sequential injection of sense and antisense strands, were sufficient to allow complete inhibition. A long interval (>1 hour) between sequential injections of sense and antisense RNA resulted in a dramatic decrease in inhibitory activity. This suggests that injected single strands may be degraded or otherwise rendered inaccessible in the absence of the complementary strand.

An issue of specificity arises when considering known cellular responses to dsRNA. Some organisms have a dsRNA-dependent protein kinase that activates a panic response mechanism[10]. Conceivably, the inventive sense+antisense synergy could reflect a non-specific potentiation of antisense effects by such a panic mechanism. This was not found to be the case: co-injection of dsRNA segments unrelated to unc-22 did not potentiate the ability of unc-22 single strands to mediate inhibition. Also investigated was whether double-stranded structure could potentiate inhibitory activity when placed in cis to a single-stranded segment. No such potentiation was seen; unrelated double-stranded sequences located 5' or 3' of a single-stranded unc-22 segment did not stimulate inhibition. Thus potentiation of gene-specific inhibition was observed only when dsRNA sequences exist within the region of homology with the target gene.

The phenotype produced by unc-22 dsRNA was specific. Progeny of injected animals exhibited behavior indistinguishable from characteristic unc-22 loss of function mutants. Target-specificity of dsRNA effects using three additional genes with well characterized phenotypes (FIG. 1 and Table 1). unc-54 encodes a body wall muscle myosin heavy chain isoform required for full muscle contraction[7,11,12], fem-1 encodes an ankyrin-repeat containing protein required in hermaphrodites for sperm production[13,14], and hlh-1 encodes a *C. elegans* homolog of the myoD family required for proper body shape and motility[15,16]. For each of these genes, injection of dsRNA produced progeny broods exhibiting the known null mutant phenotype, while the purified single strands produced no significant reduction in gene expression. With one exception, all of the phenotypic consequences of dsRNA injection were those expected from inhibition of the corresponding gene. The exception (segment unc54C, which led to an embryonic and larval arrest phenotype not seen with unc-54 null mutants) was illustrative. This segment covers the highly conserved myosin motor domain, and might have been expected to inhibit the activity of other highly related myosin heavy chain genes[17]. This interpretation would support uses of the present invention in which nucleotide sequence comparison of dsRNA and target gene show less than 100% identity. The unc54C segment has been unique in our overall experience to date: effects of 18 other dsRNA segments have all been limited to those expected from characterized null mutants.

The strong phenotypes seen following dsRNA injection are indicative of inhibitory effects occurring in a high fraction of cells. The unc-54 and hlh-1 muscle phenotypes, in particular, are known to result from a large number of defective muscle cells[11,16]. To examine inhibitory effects of dsRNA on a cellular level, a transgenic line expressing two different GFP-derived fluorescent reporter proteins in body muscle was used. Injection of dsRNA directed to gfp produced dramatic decreases in the fraction of fluorescent cells (FIG. 2). Both reporter proteins were absent from the negative cells, while the few positive cells generally expressed both GFP forms.

The pattern of mosaicism observed with gfp inhibition was not random. At low doses of dsRNA, the inventors saw frequent inhibition in the embryonically-derived muscle cells present when the animal hatched. The inhibitory effect in these differentiated cells persisted through larval growth: these cells produced little or no additional GFP as the affected animals grew. The 14 postembryonically-derived striated muscles are born during early larval stages and were more resistant to inhibition. These cells have come through additional divisions (13-14 versus 8-9 for embryonic muscles[18,19]). At high concentrations of gfp dsRNA, inhibition was noted in virtually all striated bodywall muscles, with occasional single escaping cells including cells born in embryonic or post-embryonic stages. The nonstriated vulval muscles, born during late larval development, appeared resistant to genetic inhibition at all tested concentrations of injected RNA. The latter result is important for evaluating the use of the present invention in other systems. First, it indicates that failure in one set of cells from an organism does not necessarily indicate complete non-applicability of the invention to that organism. Second, it is important to realize that not all tissues in the organism need to be affected for the invention to be used in an organism. This may serve as an advantage in some situations.

A few observations serve to clarify the nature of possible targets and mechanisms for RNA-mediated genetic inhibition in C. elegans:

First, dsRNA segments corresponding to a variety of intron and promoter sequences did not produce detectable inhibition (Table 1). Although consistent with possible inhibition at a post-transcriptional level, these experiments do not rule out inhibition at the level of the gene.

Second, dsRNA injection produced a dramatic decrease in the level of the endogenous mRNA transcript (FIG. 3). Here, a mex-3 transcript that is abundant in the gonad and early embryos[20] was targeted, where straightforward in situ hybridization can be performed[5]. No endogenous mex-3 mRNA was observed in animals injected with a dsRNA segment derived from mex-3 (FIG. 3D), but injection of purified mex-3 antisense RNA resulted in animals that retained substantial endogenous mRNA levels (FIG. 3C).

Third, dsRNA-mediated inhibition showed a surprising ability to cross cellular boundaries. Injection of dsRNA for unc-22, gfp, or lacZ into the body cavity of the head or tail produced a specific and robust inhibition of gene expression in the progeny brood (Table 2). Inhibition was seen in the progeny of both gonad arms, ruling out a transient "nicking" of the gonad in these injections. dsRNA injected into body cavity or gonad of young adults also produced gene-specific inhibition in somatic tissues of the injected animal (Table 2).

Table 3 shows that C. elegans can respond in a gene-specific manner to dsRNA encountered in the environment. Bacteria are a natural food source for C. elegans. The bacteria are ingested, ground in the animal's pharynx, and the bacterial contents taken up in the gut. The results show that E. coli bacteria expressing dsRNAs can confer specific inhibitory effects on C. elegans nematode larvae that feed on them.

Three C. elegans genes were analyzed. For each gene, corresponding dsRNA was expressed in E. coli by inserting a segment of the coding region into a plasmid construct designed for bidirectional transcription by bacteriophage T7 RNA polymerase. The dsRNA segments used for these experiments were the same as those used in previous microinjection experiments (see FIG. 1). The effects resulting from feeding these bacteria to C. elegans were compared to the effects achieved by microinjecting animals with dsRNA.

The C. elegans gene unc-22 encodes an abundant muscle filament protein. unc-22 null mutations produce a characteristic and uniform twitching phenotype in which the animals can sustain only transient muscle contraction. When wild-type animals were fed bacteria expressing a dsRNA segment from unc-22, a high fraction (85%) exhibited a weak but still distinct twitching phenotype characteristic of partial loss of function for the unc-22 gene. The C. elegans fem-1 gene encodes a late component of the sex determination pathway. Null mutations prevent the production of sperm and lead eupoid (XX) animals to develop as females, while wild type XX animals develop as hermaphrodites. When wild-type animals were fed bacteria expressing dsRNA corresponding to fem-1, a fraction (43%) exhibit a sperm-less (female) phenotype and were sterile. Finally, the ability to inhibit gene expression of a transgene target was assessed. When animals carrying a gfp transgene were fed bacteria expressing dsRNA corresponding to the gfp reporter, an obvious decrease in the overall level of GFP fluorescence was observed, again in approximately 12% of the population (see FIG. 5, panels B and C).

The effects of these ingested RNAs were specific. Bacteria carrying different dsRNAs from fem-1 and gfp produced no twitching, dsRNAs from unc-22 and fem-1 did not reduce gfp expression, and dsRNAs from gfp and unc-22 did not produce females. These inhibitory effects were apparently mediated by dsRNA: bacteria expressing only the sense or antisense strand for either gfp or unc-22 caused no evident phenotypic effects on their C. elegans predators.

Table 4 shows the effects of bathing C. elegans in a solution containing dsRNA. Larvae were bathed for 24 hours in solutions of the indicated dsRNAs (1 mg/ml), then allowed to recover in normal media and allowed to grow under standard conditions for two days. The unc-22 dsRNA was segment ds-unc22A from FIG. 1. pos-1 and sqt-3 dsRNAs were from the full length cDNA clones. pos-1 encodes an essential maternally provided component required early in embyogenesis. Mutations removing pos-1 activity have an early embryonic arrest characteristic of skn-like mutations[29,30]. Cloning and activity patterns for sqt-3 have been described[31]. C. elegans sqt-3 mutants have mutations in the col-1 collagen gene[31]. Phenotypes of affected animals are noted. Incidences of clear phenotypic effects in these experiments were 5-10% for unc-22, 50% for pos-1, and 5% for sqt-3. These are frequencies of unambiguous phenocopies; other treated animals may have had marginal defects corresponding to the target gene that were not observable. Each treatment was fully gene-specific in that unc-22 dsRNA produced only Unc-22 phenotypes, pos-1 dsRNA produced only Pos-1 phenotypes, and sqt-3 dsRNA produced only Sqt-3 phenotypes.

Some of the results described herein were published after the filing of our provisional application. Those publications and a review can be cited as Fire, A., et al. Nature, 391, 806-811, 1998; Timmons, L. & Fire, A. Nature, 395, 854, 1998; and Montgomery, M. K. & Fire, A. Trends in Genetics, 14, 255-258, 1998.

The effects described herein significantly augment available tools for studying gene function in C. elegans and other organisms. In particular, functional analysis should now be possible for a large number of interesting coding regions[21] for which no specific function have been defined. Several of these observations show the properties of dsRNA that may affect the design of processes for inhibition of gene expression. For example, one case was observed in which a nucleotide sequence shared between several myosin genes may inhibit gene expression of several members of a related gene family.

Methods of RNA Synthesis and Microinjection

RNA was synthesized from phagemid clones with T3 and T7 RNA polymerase[6], followed by template removal with two sequential DNase treatments. In cases where sense, antisense, and mixed RNA populations were to be compared, RNAs were further purified by electrophoresis on low-gelling-temperature agarose. Gel-purified products appeared to lack many of the minor bands seen in the original "sense" and "antisense" preparations. Nonetheless, RNA species accounting for less than 10% of purified RNA preparations would not have been observed. Without gel purification, the "sense" and "antisense" preparations produced significant inhibition. This inhibitory activity was reduced or eliminated upon gel purification. By contrast, sense+antisense mixtures of gel purified and non-gel-purified RNA preparations produced identical effects.

Following a short (5 minute) treatment at 68° C. to remove secondary structure, sense+antisense annealing was carried out in injection buffer[27] at 37° C. for 10-30 minutes. Formation of predominantly double stranded material was confirmed by testing migration on a standard (non-denaturing) agarose gel: for each RNA pair, gel mobility was shifted to that expected for double-stranded RNA of the appropriate length. Co-incubation of the two strands in a low-salt buffer (5 mM Tris-HCl pH 7.5, 0.5 mM EDTA) was insufficient for visible formation of double-stranded RNA in vitro. Non-annealed sense+antisense RNAs for unc22B and gfpG were tested for inhibitory effect and found to be much more active than the individual single strands, but 2-4 fold less active than equivalent pre-annealed preparations.

After pre-annealing of the single strands for unc22A, the single electrophoretic species corresponding in size to that expected for dsRNA was purified using two rounds of gel electrophoresis. This material retained a high degree of inhibitory activity.

Except where noted, injection mixes were constructed so animals would receive an average of $0.5 \times 10^6$ to $1.0 \times 10^6$ molecules of RNA. For comparisons of sense, antisense, and dsRNA activities, injections were compared with equal masses of RNA (i.e., dsRNA at half the molar concentration of the single strands). Numbers of molecules injected per adult are given as rough approximations based on concentration of RNA in the injected material (estimated from ethidium bromide staining) and injection volume (estimated from visible displacement at the site of injection). A variability of several-fold in injection volume between individual animals is possible; however, such variability would not affect any of the conclusions drawn herein.

Methods for Analysis of Phenotypes

Inhibition of endogenous genes was generally assayed in a wild type genetic background (N2). Features analyzed included movement, feeding, hatching, body shape, sexual identity, and fertility. Inhibition with gfp[27] and lacZ activity was assessed using strain PD4251. This strain is a stable transgenic strain containing an integrated array (ccIs4251) made up of three plasmids: pSAK4 (myo-3 promoter driving mitochondrially targeted GFP), pSAK2 (myo-3 promoter driving a nuclear targeted GFP-LacZ fusion), and a dpy-20 subclone[26] as a selectable marker. This strain produces GFP in all body muscles, with a combination of mitochondrial and nuclear localization. The two distinct compartments are easily distinguished in these cells, allowing a facile distinction between cells expressing both, either, or neither of the original GFP constructs.

Gonadal injection was performed by inserting the microinjection needle into the gonadal syncitium of adults and expelling 20-100 pl of solution (see Reference 25). Body cavity injections followed a similar procedure, with needle insertion into regions of the head and tail beyond the positions of the two gonad arms. Injection into the cytoplasm of intestinal cells was another effective means of RNA delivery, and may be the least disruptive to the animal. After recovery and transfer to standard solid media, injected animals were transferred to fresh culture plates at 16 hour intervals. This yields a series of semi-synchronous cohorts in which it was straightforward to identify phenotypic differences. A characteristic temporal pattern of phenotypic severity is observed among progeny. First, there is a short "clearance" interval in which unaffected progeny are produced. These include impermeable fertilized eggs present at the time of injection. After the clearance period, individuals are produced which show the inhibitory phenotype., After injected animals have produced eggs for several days, gonads can in some cases "revert" to produce incompletely affected or phenotypically normal progeny.

Additional Description of the Results

FIG. 1 shows genes used to study RNA-mediated genetic inhibition in C. elegans. Intron-exon structure for genes used to test RNA-mediated inhibition are shown (exons: filled boxes; introns: open boxes; 5' and 3' untranslated regions: shaded; sequence references are as follows: unc-22[9], unc-54[12], fem-1[14], and hlh-1[15]). These genes were chosen based on: (1) a defined molecular structure, (2) classical genetic data showing the nature of the null phenotype. Each segment tested for inhibitory effects is designated with the name of the gene followed by a single letter (e.g., unc22C). Segments derived from genomic DNA are shown above the gene, segments derived from cDNA are shown below the gene. The consequences of injecting double-stranded RNA segments for each of these genes is described in Table 1. dsRNA sequences from the coding region of each gene produced a phenotype resembling the null phenotype for that gene.

The effects of inhibitory RNA were analyzed in individual cells (FIG. 2, panels A-H). These experiments were carried out in a reporter strain (called PD4251) expressing two different reporter proteins: nuclear GFP-LacZ and mitochondrial GFP, both expressed in body muscle. The fluorescent nature of these reporter proteins allowed us to examine individual cells under the fluorescence microscope to determine the extent and generality of the observed inhibition of gene. ds-unc22A RNA was injected as a negative control. GFP expression in progeny of these injected animals was not affected. The GFP patterns of these progeny appeared identical to the parent strain, with prominent fluorescence in nuclei (the nuclear localized GFP-LacZ) and mitochondria (the mitochondrially targeted GFP): young larva (FIG. 2A), adult (FIG. 2B), and adult body wall at high magnification (FIG. 2C).

In contrast, the progeny of animals injected with ds-gfpG RNA are affected (FIGS. 2D-F). Observable GFP fluorescence is completely absent in over 95% of the cells. Few active cells were seen in larvae (FIG. 2D shows a larva with one active cell; uninjected controls show GFP activity in all 81 body wall muscle cells). Inhibition was not effective in all tissues: the entire vulval musculature expressed active GFP in an adult animal (FIG. 2E). Rare GFP positive body wall muscle cells were-also seen adult animals (two active cells are shown in FIG. 2F). Inhibition was target specific (FIGS. 2G-I). Animals were injected with ds-lacZL RNA, which should affect the nuclear but not the mitochondrial reporter construct. In the animals derived from this injection, mitochondrial-targeted GFP appeared unaffected while the nuclear-targeted GFP-LacZ was absent from almost all cells (larva in FIG. 2G). A typical adult lacked nuclear GFP-LacZ in almost all body-wall muscles but retained activity in vulval muscles (FIG. 2H). Scale bars in FIG. 2 are 20 μm.

The effects of double-stranded RNA corresponding to mex-3 on levels of the endogenous mRNA was shown by in situ hybridization to embryos (FIG. 3, panels A-D). The 1262 nt mex-3 cDNA clone[20] was divided into two segments, mex-3A and mex-3B with a short (325 nt) overlap. Similar results were obtained in experiments with no overlap between inhibiting and probe segments. mex-3B antisense or dsRNA was injected into the gonads of adult animals, which were maintained under standard culture conditions for 24 hours before fixation and in situ hybridization (see Reference 5). The mex-3B dsRNA produced 100% embryonic arrest, while >90% of embryos from the antisense injections hatched. Antisense probes corresponding to mex-3A were used to assay distribution of the endogenous mex-3 mRNA (dark stain). Four-cell stage embryos were assayed; similar results were observed from the 1 to 8 cell stage and in the germline of injected adults. The negative control (the absence of hybridization probe) showed a lack of staining (FIG. 3A). Embryos from uninjected parents showed a normal pattern of endogenous mex-3 RNA (FIG. 3B). The observed pattern of mex-3 RNA was as previously described in Reference 20. Injection of purified mex-3B antisense RNA produced at most a modest effect: the resulting embryos retained mex-3 mRNA, although levels may have been somewhat less than wild type (FIG. 3C). In contrast, no mex-3 RNA was detected in embryos from parents injected with dsRNA corresponding to mex-3B (FIG. 3D). The scale of FIG. 3 is such that each embryo is approximately 50 μm in length.

Gene-specific inhibitory activity by unc-22A RNA was measured as a function of RNA structure and concentration (FIG. 4). Purified antisense and sense RNA from unc22A were injected individually or as an annealed mixture. "Control" was an unrelated dsRNA (gfpG). Injected animals were transferred to fresh culture plates 6 hours (columns labeled 1), 15 hours (columns labeled 2), 27 hours (columns labeled 3), 41 hours (columns labeled 4), and 56 hours (columns labeled 5) after injection. Progeny grown to adulthood were scored for movement in their growth environment, then examined in 0.5 mM levamisole. The main graph indicates fractions in each behavioral class. Embryos in the uterus and already covered with an eggshell at the time of injection were not affected and, thus, are not included in the graph. The bottom-left diagram shows the genetically derived relationship between unc-22 gene dosage and behavior based on analyses of unc-22 heterozygotes and polyploids[8,3].

FIGS. 5 A-C show a process and examples of genetic inhibition following ingestion by C. elegans of dsRNAs from expressing bacteria. A general strategy for production of dsRNA is to clone segments of interest between flanking copies of the bacteriophage T7 promoter into a bacterial plasmid construct (FIG. 5A). A bacterial strain (BL21/DE3)[28] expressing the T7 polymerase gene from an inducible (Lac) promoter was used as a host. A nuclease-resistant dsRNA was detected in lysates of transfected bacteria. Comparable inhibition results were obtained with the two bacterial expression systems. A GFP-expressing C. elegans strain, PD4251 (see FIG. 2), was fed on a native bacterial host. These animals show a uniformly high level of GFP fluorescence in body muscles (FIG. 5B). PD4251 animals were also reared on a diet of bacteria expressing dsRNA corresponding to the coding region for gfp. Under the conditions of this experiment, 12% of these animals showed dramatic decreases in GFP (FIG. 5C). As an alternative strategy, single copies of the T7 promoter were used to drive expression of an inverted-duplication for a segment of the target gene, either unc-22 or gfp. This was comparably effective.

All references (e.g., books, articles, applications, and patents) cited in this specification are indicative of the level of skill in the art and their disclosures are incorporated herein in their entirety.

1. Izant, J. & Weintraub, H. *Cell* 36, 1007-1015 (1984).
2. Nellen, W. & Lichtenstein, C. *TIBS* 18, 419-423 (1993).
3. Fire, A., et al. *Development* 113, 503-514 (1991).
4. Guo, S. & Kemphues, K. *Cell* 81, 611-620 (1995).
5. Seydoux, G. & Fire, A. *Development* 120, 2823-2834 (1994).
6. Ausubel, F., et al. *Current Protocols in Molecular Biology*, John Wiley N.Y. (1990).
7. Brenner, S. *Genetics* 77, 71-94 (1974).
8. Moerman, D. & Baillie, D. *Genetics* 91, 95-104 (1979).
9. Benian, G., et al. *Genetics* 134, 1097-1104 (1993).
10. Proud, C. *TIBS* 20, 241-246 (1995).
11. Epstein H., et al. *J. Mol. Biol.* 90 291-300 (1974).
12. Karn, J., et al. *Proc. Natl. Acad. Sci. (U.S.A.)* 80, 4253-4257 (1983).
13. Doniach, T. & Hodgkin J. A. *Dev. Biol.* 106, 223-235 (1984).
14. Spence, A., et al. *Cell* 60, 981-990 (1990).
15. Krause, M., et al. *Cell* 63, 907-919 (1990).
16. Chen, L., et al. *Development,* 120, 1631-1641 (1994).
17. Dibb, N. J., et al. *J. Mol. Biol.* 205, 603-613 (1989).
18. Sulston, J., et al. *Dev. Biol.* 100, 64-119 (1983).
19. Sulston, J. & Horvitz, H. *Dev. Biol.* 82, 41-55 (1977).
20. Draper B. W., et al. *Cell* 87, 205-216 (1996).
21. Sulston, J., et al. *Nature* 356, 37-41 (1992).
22. Matzke, M. & Matzke, A. *Plant Physiol.* 107, 679-685 (1995).
23. Ratcliff, F., et al. *Science* 276, 1558-1560 (1997).
24. Latham, K. *Trends in Genetics* 12,134-138 (1996).
25. Mello, C. & Fire, A. *Methods in Cell Biology* 48, 451-482 (1995).
26. Clark, D., et al. *Mol. Gen. Genet.* 247, 367-378 (1995).
27. Chalfie, M., et al. *Science* 263, 802-805 (1994).
28. Studier, F., et al. *Methods in Enzymology* 185, 60-89 (1990).
29. Bowerman, B., et al. *Cell* 68, 1061-1075 (1992).
30. Mello, C. C., et al. *Cell* 70, 163-176 (1992).
31. van der Keyl, H., et al. *Develop. Dynamics* 201, 86-94 (1994).

32. Goeddel, D. V. *Gene Expression Technology*, Academic Press, 1990.
33. Kriegler, M. *Gene Transfer and Expression*, Stockton Press, 1990.
34. Murray, E. J. *Gene Transfer and Expression Protocols*, Humana Press, 1991.

TABLE 1

Effects of sense, antisense, and mixed RNAs on progeny of injected animals.

| Gene and Segment | | Size | Injected RNA | F1 Phenotype |
|---|---|---|---|---|
| unc-22 | | | | unc-22 null mutants: strong twitchers[7,8] |
| unc22A[a] | exon 21-22 | 742 | sense | wild type |
| | | | antisense | wild type |
| | | | sense + antisense | strong twitchers (100%) |
| unc22B | exon 27 | 1033 | sense | wild type |
| | | | antisense | wild type |
| | | | sense + antisense | strong twitchers (100%) |
| unc22C | exon 21-22[b] | 785 | sense + antisense | strong twitchers (100%) |
| fem-1 | | | | fem-1 null mutants: female (no sperm)[13] |
| fem1A | exon 10[c] | 531 | sense | hermaphrodite (98%) |
| | | | antisense | hermaphrodite (>98%) |
| | | | sense + antisense | female (72%) |
| fem1B | intron 8 | 556 | sense + antisense | hermaphrodite (>98%) |
| unc-54 | | | | unc-54 null mutants: paralyzed[7,11] |
| unc54A | exon 6 | 576 | sense | wild type (100%) |
| | | | antisense | wild type (100%) |
| | | | sense + antisense | paralyzed (100%)[d] |
| unc54B | exon 6 | 651 | sense | wild type (100%) |
| | | | antisense | wild type (100%) |
| | | | sense + antisense | paralyzed (100%)[d] |
| unc54C | exon 1-5 | 1015 | sense + antisense | arrested embryos and larvae (100%) |
| unc54D | promoter | 567 | sense + antisense | wild type (100%) |
| unc54E | intron 1 | 369 | sense + antisense | wild type (100%) |
| unc54F | intron 3 | 386 | sense + antisense | wild type (100%) |
| hlh-1 | | | | hlh-1 null mutants: lumpy-dumpy larvae[16] |
| hlh1A | exons 1-6 | 1033 | sense | wild type (<2% lpy-dpy) |
| | | | antisense | wild type (<2% lpy-dpy) |
| | | | sense + antisense | lpy-dpy larvae (>90%)[e] |
| hlh1B | exons 1-2 | 438 | sense + antisense | lpy-dpy larvae (>80%)[e] |
| hlh1C | exons 4-6 | 299 | sense + antisense | lpy-dpy larvae (>80%)[e] |
| hlh1D | intron 1 | 697 | sense + antisense | wild type (<2% lpy-dpy) |
| myo-3 driven GFP transgenes[f] | | | | |
| myo-3::NLS::gfp::lacZ | | | | makes nuclear GFP in body muscle |
| gfpG | exons 2-5 | 730 | sense | nuclear GFP-LacZ pattern of parent strain |
| | | | antisense | nuclear GFP-LacZ pattern of parent strain |
| | | | sense + antisense | nuclear GFP-LacZ absent in 98% of cells |
| lacZL | exon 12-14 | 830 | sense + antisense | nuclear GFP-LacZ absent in >95% of cells |
| myo-3::MtLS::gfp | | | | makes mitochondrial GFP in body muscle |
| gfpG | exons 2-5 | 730 | sense | mitochondrial GFP pattern of parent strain |
| | | | antisense | mitochondrial GFP pattern of parent strain |
| | | | sense + antisense | mitochondrial GFP absent in 98% of cells |

TABLE 1-continued

Effects of sense, antisense, and mixed RNAs on progeny of injected animals.

| Gene and Segment | | Size | Injected RNA | F1 Phenotype |
|---|---|---|---|---|
| lacZL | exon 12-14 | 830 | sense + antisense | mitochondrial GFP pattern of parent strain |

Legend of Table 1

Each RNA was injected into 6-10 adult hermaphrodites ($0.5-1\times10^6$ molecules into each gonad arm). After 4-6 hours (to clear pre-fertilized eggs from the uterus) injected animals were transferred and eggs collected for 20-22 hours. Progeny phenotypes were scored upon hatching and subsequently at 12-24 hour intervals.

a: To obtain a semi-quantitative assessment of the relationship between RNA dose and phenotypic response, we injected each unc22A RNA preparation at a series of different concentrations. At the highest dose tested ($3.6\times10^6$ molecules per gonad), the individual sense and antisense unc22A preparations produced some visible twitching (1% and 11% of progeny respectively). Comparable doses of ds-unc22A RNA produced visible twitching in all progeny, while a 120-fold lower dose of ds-unc22A RNA produced visible twitching in 30% of progeny.

b: unc22C also carries the intervening intron (43 nt).

c: fem1A also carries a portion (131 nt) of intron 10.

d: Animals in the first affected broods (laid at 4-24 hours after injection) showed movement defects indistinguishable from those of null mutants in unc-54. A variable fraction of these animals (25-75%) failed to lay eggs (another phenotype of unc-54 null mutants), while the remainder of the paralyzed animals were egg-laying positive. This may indicate partial inhibition of unc-54 activity in vulval muscles. Animals from later broods frequently exhibit a distinct partial loss-of-function phenotype, with contractility in a subset of body wall muscles.

e: Phenotypes of hlh-1 inhibitory RNA include arrested embryos and partially elongated L1 larvae (the hlh-1 null phenotype) seen in virtually all progeny from injection of ds-hlh1A and about half of the affected animals from-ds-hlh1B and ds-hlh1C) and a set of less severe defects (seen with the remainder of the animals from ds-hlh1B and ds-hlh1C). The less severe phenotypes are characteristic of partial loss of function for hlh-1.

f: The host for these injections, PD4251, expresses both mitochondrial GFP and nuclear GFP-LacZ. This allows simultaneous assay for inhibition of gfp (loss of all fluorescence) and lacZ (loss of nuclear fluorescence). The table describes scoring of animals as L1 larvae. ds-gfpG caused a loss of GFP in all but 0-3 of the 85 body muscles in these larvae. As these animals mature to adults, GFP activity was seen in 0-5 additional bodywall muscles and in the eight vulval muscles.

TABLE 2

Effect of injection point on genetic inhibition in injected animals and their progeny.

| dsRNA | Site of injection | Injected animal phenotype | Progeny Phenotype |
|---|---|---|---|
| None | gonad or body cavity | no twitching | no twitching |
| None | gonad or body cavity | strong nuclear & mitochondrial GFP | strong nuclear & mitochondrial GFP |

TABLE 2-continued

Effect of injection point on genetic inhibition in injected animals and their progeny.

| dsRNA | Site of injection | Injected animal phenotype | Progeny Phenotype |
|---|---|---|---|
| unc22B | Gonad | weak twitchers | strong twitchers |
| unc22B | Body Cavity Head | weak twitchers | strong twitchers |
| unc22B | Body Cavity Tail | weak twitchers | strong twitchers |
| gfpG | Gonad | lower nuclear & mitochondrial GFP | rare or absent nuclear & mitochondrial GFP |
| gfpG | Body Cavity Tail | lower nuclear & mitochondrial GFP | rare or absent nuclear & mitochondrial GFP |
| lacZL | Gonad | lower nuclear GFP | rare or absent nuclear GFP |
| lacZL | Body Cavity Tail | lower nuclear GFP | rare or absent nuclear GFP |

TABLE 3

*C. elegans* can respond in a gene-specific manner to environmental dsRNA.

| Bacterial Food | Movement | Germline Phenotype | GFP-Transgene Expression |
|---|---|---|---|
| BL21(DE3) | 0% twitch | <1% female | <1% faint GFP |
| BL21(DE3) [fem-1 dsRNA] | 0% twitch | 43% female | <1% faint GFP |
| BL21(DE3) [unc22 dsRNA] | 85% twitch | <1% female | <1% faint GFP |
| BL21(DE3) [gfp dsRNA] | 0% twitch | <1% female | 12% faint GFP |

TABLE 4

Effects of bathing *C. elegans* in a solution containing dsRNA.

| dsRNA | Biological Effect |
|---|---|
| unc-22 | Twitching (similar to partial loss of unc-22 function) |
| pos-1 | Embryonic arrest (similar to loss of pos-1 function) |
| sqt-3 | Shortened body (Dpy) (similar to partial loss of sqt-3 function) |

In Table 2, gonad injections were carried out into the GFP reporter strain PD4251, which expresses both mitochondrial GFP and nuclear GFP-LacZ. This allowed simultaneous assay of inhibition with gfp (fainter overall fluorescence), lacZ (loss of nuclear fluorescence), and unc-22 (twitching). Body cavity injections were carried out into the tail region, to minimize accidental injection of the gonad; equivalent results have been observed with injections into the anterior region of the body cavity. An equivalent set of injections was also performed into a single gonad arm. For all sites of injection, the entire progeny brood showed phenotypes identical to those described in Table 1. This included progeny produced from both injected and uninjected gonad arms. Injected animals were scored three days after recovery and showed somewhat less dramatic phenotypes than their progeny. This could in part be due to the persistence of products already present in the injected adult. After ds-unc22B injection, a fraction of the injected animals twitch weakly under standard growth conditions (10 out of 21 animals). Levamisole treatment led to twitching of 100% (21/21) of these animals. Similar effects were seen with ds-unc22A. Injections of ds-gfpG or ds-lacZL produced a dramatic decrease (but not elimination) of the corresponding GFP reporters. In some cases, isolated cells or parts of animals retained strong GFP activity. These were most frequently seen in the anterior region and around the vulva. Injections of ds-gfpG and ds-lacZL produced no twitching, while injections of ds-unc22A produced no change in GFP fluorescence pattern.

While the present invention has been described in connection with what is presently considered to be practical and preferred embodiments, it is understood that the invention is not to be limited or restricted to the disclosed embodiments but, on the contrary, is intended to cover various modifications and equivalent arrangements included within the spirit and scope of the appended claims.

Thus it is to be understood that variations in the described invention will be obvious to those skilled in the art without departing from the novel aspects of the present invention and such variations are intended to come within the scope of the present invention.

We claim:

1. A method to inhibit expression of a target gene in a cell in a multicellular animal comprising providing at least one ribonucleic acid (RNA) to the cell in an amount sufficient to inhibit the expression of the target gene, wherein the RNA comprises or forms a double-stranded structure containing a first strand consisting essentially of a ribonucleotide sequence which corresponds to a nucleotide sequence of the target gene and a second strand consisting essentially of a ribonucleotide sequence which is complementary to the nucleotide sequence of the target gene, wherein the first and the second ribonucleotide sequences are separate complementary sequences that hybridize to each other to form said double-stranded structure, and the RNA comprising the double-stranded structure inhibits expression of the target gene, and wherein said animal is selected from the group consisting of worms and insects.

2. The method of claim 1, wherein said multicellular animal has a digestive system, and wherein the RNA is provided to said animal by feeding said animal a second organism.

3. The method of claim 2, wherein said second organism is engineered to produce said RNA from an expression construct.

4. A method to inhibit expression of a target gene in a cell in an animal comprising:
   (a) isolating the cell from said animal;
   (b) introducing an expression construct into said cell encoding an RNA comprising a double-stranded structure containing a first strand consisting essentially of a ribonucleotide sequence which corresponds to a nucleotide sequence of the target gene and a second strand consisting essentially of a ribonucleotide sequence which is complementary to the nucleotide sequence of the target gene, wherein the first and the second ribonucleotide sequences are separate sequences that hybridize to each other to form said double-stranded structure, and
   (c) subsequently introducing said cell into said animal, wherein said RNA comprising the double-stranded structure inhibits expression of the target gene in said cell in said animal.

5. The method of claim 4, wherein said cell is at risk for infection by a pathogen.

6. The method of claim 4, wherein said cell is a human cell at risk for infection by a virus.

7. A method to inhibit expression of a target gene in a cell in an invertebrate animal comprising providing at least one ribonucleic acid (RNA) to the cell in an amount sufficient to inhibit the expression of the target gene, wherein said RNA is provided to the cell by synthesizing said RNA in said cell, wherein the RNA comprises or forms a double-stranded structure containing a first strand consisting essentially of a ribonucleotide sequence which corresponds to a nucleotide sequence of the target gene and a second strand consisting essentially of a ribonucleotide sequence which is complementary to the nucleotide sequence of the target gene, wherein the first and the second ribonucleotide sequences are complementary sequences that hybridize to each other to form said double-stranded structure and the RNA comprising the double-stranded structure inhibits expression of the target gene, and wherein the RNA is a double-stranded molecule containing two separate complementary RNA strands.

8. The method of claim 7, wherein said RNA is provided to the cell by introducing an expression construct that synthesizes said RNA in said cell.

9. The method of claim 8, wherein said invertebrate animal has a digestive system, and wherein said expression construct is orally administered to said animal such that the expression construct is introduced into the cell, thereby inhibiting expression of the target gene.

10. The method of claim 7, wherein said invertebrate animal has a digestive system, and wherein the RNA is provided to said animal by feeding a second organism.

11. The method of claim 10, wherein said second organism is engineered to produce said RNA from an expression construct.

12. A method to inhibit expression of a target gene in a cell comprising:
(a) isolating the cell from an animal;
(b) contacting the cell with at least one ribonucleic acid (RNA) comprising a double-stranded structure containing a first strand consisting essentially of a ribonucleotide sequence which corresponds to a nucleotide sequence of the target gene and a second strand consisting essentially of a ribonucleotide sequence which is complementary to the nucleotide sequence of the target gene, wherein the first and the second ribonucleotide sequences are separate sequences that hybridize to each other to form said double-stranded structure, and
(c) subsequently introducing said cell into said animal, wherein said RNA comprising the double-stranded structure inhibits expression of the target gene in said cell.

13. The method of claim 7, wherein said invertebrate animal has a digestive system, and wherein a nucleic acid encoding said RNA is orally administered to said animal for synthesis of said RNA in the cell, thereby inhibiting expression of the target gene.

14. The method of claim 1, wherein said RNA is provided to the cell by introducing an expression construct into said cell.

15. The method of claim 14, wherein said expression construct is directly injected into said animal in the vicinity of said cell such that the construct is introduced into the cell, thereby inhibiting expression of the target gene.

16. The method of claim 14, wherein said multicellular animal has a body cavity or interstitial space, and said expression construct is introduced into a body cavity or interstitial space of said animal such that the expression construct is introduced into the cell, thereby inhibiting expression of the target gene.

17. The method of claim 14, wherein said multicellular animal has a digestive system, and wherein said expression construct is orally administered to said animal such that the expression construct is introduced into the cell, thereby inhibiting expression of the target gene.

18. The method of claim 1 wherein said worm is a nematode.

19. The method of claim 1 wherein said insect is Drosophila.

* * * * *